(12) United States Patent
Biesecker et al.

(10) Patent No.: US 6,465,189 B1
(45) Date of Patent: *Oct. 15, 2002

(54) SYSTEMATIC EVOLUTION OF LIGANDS BY EXPONENTIAL ENRICHMENT: BLENDED SELEX

(75) Inventors: Greg Biesecker; Sumedha Jayasena; Larry Gold; Drew Smith, all of Boulder; Gary Kirschenheuter, Arvada, all of CO (US)

(73) Assignee: Gilead Sciences, Inc., Foster City, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 09/606,477

(22) Filed: Jun. 29, 2000

Related U.S. Application Data

(63) Continuation of application No. 08/956,699, filed on Oct. 23, 1997, now Pat. No. 6,083,696, which is a continuation of application No. 08/234,997, filed on Apr. 28, 1994, now Pat. No. 5,683,867, application No. 09/606,477, which is a continuation-in-part of application No. 08/119,507, filed on Feb. 22, 1994, now Pat. No. 5,472,841, and a continuation-in-part of application No. 08/123,935, filed on Sep. 17, 1993, now abandoned, and a continuation-in-part of application No. 08/117,991, filed on Sep. 8, 1993, and a continuation-in-part of application No. 07/714,131, filed on Jun. 10, 1991, now Pat. No. 5,475,096, which is a continuation-in-part of application No. 07/536,428, filed on Jun. 11, 1990, now abandoned.

(51) Int. Cl.[7] ............... C12Q 1/68; C12P 19/34; C07H 21/04; C07H 21/02
(52) U.S. Cl. ............... 435/6; 435/91.2; 536/23.1; 536/25.4
(58) Field of Search ............... 435/6, 91.2; 536/22.1, 536/23.1, 25.4

(56) References Cited

U.S. PATENT DOCUMENTS

| | | | | |
|---|---|---|---|---|
| 5,270,163 | A | 12/1993 | Gold et al. | 435/6 |
| 5,683,867 | A | * 11/1997 | Biesecker et al. | 435/6 |
| 5,705,337 | A | * 1/1998 | Gold et al. | 435/6 |
| 5,723,323 | A | 3/1998 | Kauffman et al. | 435/6 |
| 5,998,142 | A | * 12/1999 | Gold et al. | 435/6 |
| 6,083,696 | A | * 7/2000 | Biesecker et al. | 435/6 |

FOREIGN PATENT DOCUMENTS

| | | |
|---|---|---|
| GB | 2 183 661 A | 6/1987 |
| WO | WO89/06694 | 7/1989 |
| WO | WO91/14696 | 10/1991 |
| WO | WO91/19813 | 12/1991 |
| WO | WO92/14843 | 9/1992 |
| WO | WO95/16788 | 6/1995 |

OTHER PUBLICATIONS

Barrett (1978) Agents and Actions 8:11.
Bonney (1989) J. Cell Biochem 39:47.
Dewald et al. (1975) J. Exp. Med. 141:709.
Ellington & Szostak (1990) Abstract of papers presented at the 1990 meeting on RNA Processing, Cold Spring Harbor Laboratory, Cold Spring Harbor, NY, p. 84.
Frojmovic et al. (1991) Blood 78:369.
Hemmi et al. (1985) Biochemistry 24:1841.
Joyce (1989) Gene 82:83.
Joyce & Inoue (1989) Nucleic Acids Res. 17:711.
Kaplan et al. (1973) J. Lab. Clin. Med. 82:349.
Kinzler & Vogelstein (1989) Nucleic Acids Res. 17:3645.
Kramer et al. (1974) J. Mol. Biol. 89:719.
Levisohn & Spiegelman (1969) Proc. Natl. Acad. Sci. USA 63:805.
Levisohn & Speigelman (1968) Proc. Natl. Acad. Sci. USA 60:866.
Loftus et al. (1990) Science 249:915.
Oleksyszyn and Powers (1989) Biochem. and Biophys. Res. Comm. 161:143.
Oliphant et al. (1989) Mol. Cell. Biol. 9:2944.
Oliphant et al. (1986) Gene 44:177.
Oliphant & Struhl (1988) Nucleic Acids Res. 16:7673.
Oliphant & Struhl (1987) Methods in Enzymology 155:568.
Phillips et al (1988) Blood 71:831.
Robertson & Joyce (1990) Nature 344:467.
Sanders and Moore (1983) Am. Rev. Respir. Dis. 127:554.
Szostak, "Structure and Activity of Ribozymes" in *Redesigning the Molecules of Life*, (S.A. Benner ed.)Springer–Verlage Berline Heidelberg, pp. 87–113 (1988).
Thiesen & Bach (1990) Nucleic Acids Res. 18:3203.
Ware and Heistad (1993) N. Eng. J. Med. 328:628.
Weiland et al. (1986) Am. Rev. Respir. Dis. 133:218.

\* cited by examiner

*Primary Examiner*—Stephanie Zitomer
(74) *Attorney, Agent, or Firm*—Swanson & Bratschun, L.L.C.

(57) ABSTRACT

A method is described for generating blended nucleic acid ligands containing non-nucleic acid functional units. Specifically, a SELEX identified RNA ligand to the integrin gpIIbIIIa is conjugated to the peptide Gly-Arg-Gly-Asp-Thr-Pro (SEQ ID NO:1). This blended RNA ligand inhibits the biological activity of gpIIbIIIa with high specificity. Also described is a single-stranded DNA ligand to elastase coupled to N-methoxysuccinyl-Ala-Ala-Pro-Val-chloromethyl ketone (SEQ ID NO:2). This elastase blended nucleic acid ligand inhibits the biological activity of elastase.

12 Claims, 19 Drawing Sheets

Urokinase Activity

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: single
      (D) TOPOLOGY: linear (xi) SEQUENCE DESCRIPTION: SEQ ID NO: 1:

Gly Arg Gly Asp Thr Pro
1            5

(2) INFORMATION FOR SEQ ID NO: 2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ix) FEATURE:
      (A) NAME/KEY: Xaa
      (B) LOCATION: 1
      (D) OTHER INFORMATION: This symbol stands for N-methylsuccinylalanine (ix) FEATURE:
      (A) NAME/KEY: Xaa
      (B) LOCATION: 4
      (D) OTHER INFORMATION: Valine chloromethyl ketone (xi) SEQUENCE DESCRIPTION: SEQ ID NO: 2:

Xaa Ala Pro Xaa
1

(2) INFORMATION FOR SEQ ID NO: 3:

(i) SEQUENCE CHARACTERISTICS:
      (A) LENGTH: 59 nucleotides

-continued

```
            (B) TYPE: nucleic acid
            (C) STRANDEDNESS: single
            (D) TOPOLOGY: linear (xi) SEQUENCE DESCRIPTION: SEQ ID NO: 3:

TAGCGATACT GCGTGGGTTG GGGCGGGTAG GGCCAGCAGT CTCGTGCGGT          50

ACTTGAGCA                                                      59

(2) INFORMATION FOR SEQ ID NO: 4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: Xaa
            (B) LOCATION: 1
            (D) OTHER INFORMATION:  N-methyoxysuccinyl alanine (ix) FEATURE:
            (A) NAME/KEY: Xaa
            (B) LOCATION: 4
            (D) OTHER INFORMATION:  Valine p-nitroanilide (xi) SEQUENCE DESCRIPTION: SEQ ID NO: 4:

Xaa Ala Pro Xaa
1

(2) INFORMATION FOR SEQ ID NO: 5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ix) FEATURE:
            (A) NAME/KEY: Xaa
            (B) LOCATION: 1
            (D) OTHER INFORMATION:  N-methyoxysuccinyl alanine (xi) SEQUENCE DESCRIPTION: SEQ ID NO: 5:

Xaa Ala Pro Val
1
```

SYSTEMATIC EVOLUTION OF LIGANDS BY EXPONENTIAL ENRICHMENT: BLENDED SELEX

RELATED APPLICATIONS

This application is a continuation of U.S. patent application Ser. No. 08/956,699, filed Oct. 23, 1997 now U.S. Pat. No. 6,083,696, which is a continuation of U.S. patent application Ser. No. 08/234,997, filed Apr. 28, 1994, now U.S. Pat. No. 5,683,867, both entitled "Systematic Evolution of Ligands by Exponential Enrichment: Blended SELEX." This application is also a continuation-in-part of U.S. patent application Ser. No. 07/714,131, filed Jun. 10, 1991, entitled "Nucleic Acid Ligands," now U.S. Pat. No. 5,475,096, which was filed as a continuation-in-part of U.S. patent application Ser. No. 07/536,428, filed Jun. 11, 1990, entitled "Systematic Evolution of Ligands by Exponential Enrichment," now abandoned. This application is also a continuation-in-part of U.S. patent application Ser. Nos. 08/117,991, filed Sep. 8, 1993, entitled "High Affinity Nucleic Acid Ligands Containing Modified Nucleotides," now abandoned, U.S. patent application Ser. No. 08/123,935, filed Sep. 17, 1993, entitled "Photoselection of Nucleic Acid Ligands," now abandoned, and U.S. patent application Ser. No. 08/199,507, filed Feb. 22, 1994, entitled "Methods for Identifying Nucleic Acid Ligands of Human Neutrophil Elastase," now U.S. Pat. No. 5,472,841.

FIELD OF THE INVENTION

Described herein is a method of combining nucleic acids with other functional units for generation of high affinity ligands. The method of this invention takes advantage of the method for identifying nucleic acid ligands referred to as SELEX. SELEX is an acronym for Systematic Evolution of Ligands by EXponential enrichment. The method presented herein is termed blended SELEX. Examples of functional units that may be coupled to nucleic acids include proteins, peptides, photoreactive groups, chemically-reactive groups, active site directed compounds, lipids, biotin, and fluorescent compounds. The blended nucleic acid ligands of the present invention consist of at least one nucleic acid ligand unit and at least one functional unit. The nucleic acid ligand unit(s) of the blended nucleic acid ligand serve in whole or in part as ligands to a given target. The functional unit(s) can be designed to serve in a large variety of functions. For example, the functional unit may independently or in combination with the nucleic acid ligand have specific affinity for the target, and in some cases may be a ligand to a different site of interaction with the target than the nucleic acid ligand. The functional unit(s) may be added which covalently react and couple the ligand to the target molecule, catalytic groups may be added to aid in the selection of protease or nuclease activity, and reporter molecules such as biotin- or fluorescence-tagged oligonucleotides may be added for use as diagnostic reagents.

BACKGROUND OF THE INVENTION

The SELEX method (hereinafter termed SELEX), was first described in U.S. application Ser. No 07/536,428, filed Jun. 11, 1990, entitled "Systematic Evolution of Ligands By Exponential Enrichment," now abandoned. U.S. Pat. No. 5,475,096, entitled "Nucleic Acid Ligands," and U.S. Pat. No. 5,270,163, entitled "Methods for Identifying Nucleic Acid Ligands," further disclose the basic SELEX process. Each of these applications are herein specifically incorporated by reference. The SELEX process provides a class of products which are referred to as nucleic acid ligands, such ligands having, a unique sequence, and which have the property of binding specifically to a desired target compound or molecule. Each SELEX-identified nucleic acid ligand is a specific ligand of a given target compound or molecule. SELEX is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size can serve as targets.

The SELEX method involves selection from a mixture of candidates and step-wise iterations of binding, partitioning, and amplification, using the same general selection theme, to achieve virtually any desired criterion of binding affinity and selectivity. Starting from a mixture of nucleic acids, preferably comprising a segment of randomized sequence, the method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired. A variety of techniques can be used to partition members in the pool of nucleic acids that have a higher affinity to the target than the bulk of the nucleic acids in the mixture.

While not bound by theory, SELEX is based on the inventors' insight that within a nucleic acid mixture containing a large number of possible sequences and structures there is a wide range of binding affinities for a given target. A nucleic acid mixture comprising, for example, a 20 nucleotide randomized segment, can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection, partition and amplification are repeated until a desired goal is achieved. In the most general case, selection/partition/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/partition/amplification iterations.

For target molecules which are nucleic acid binding proteins, evolved SELEX ligands may be homologous to the natural ligand since the nucleic acid binding protein target has evolved naturally to present side-chain and/or mainchain atoms with the correct geometry to interact with nucleic acids. Non-nucleic acid binding proteins which have evolved to bind poly-anions such as sulfated glycans (e.g., heparin), or to bind phospholipids or phosphosugars, also have sites into which nucleic acids can fit and make contacts analogous with the natural ligands and/or substrates.

For certain target molecules where the natural ligand is not a poly-anion, it can be more difficult (but still likely with relatively more rounds of SELEX) to identify oligonucleotides that fit into the substrate or ligand site. For instance, the binding pocket of trypsin contains a carboxyl group which interacts during catalysis with a lysine or arginine residue on the substrate. An oligonucleotide may not fit into this specific catalytic site because it would not contain a positively charged counter ion. Basic SELEX evolution of oligonucleotide ligands to such a target molecule may result in ligands to a site(s) distant from the substrate site, since the probability of recovering ligands to the substrate site may be low.

The basic SELEX method may be modified to achieve specific objectives. For example, U.S. Pat. No. 5,707,796, entitled "Method for Selecting Nucleic Acids on the Basis of Structure," describes the use of SELEX in conjunction with gel electrophoresis to select nucleic acid molecules with specific structural characteristics, such as bent DNA. U.S. Pat. No. 5,763,177, entitled "Photoselection of Nucleic Acid Ligands," describes a SELEX based method for selecting nucleic acid ligands containing photoreactive groups capable of binding and/or photocrosslinking to and/or photoinactivating a target molecule. U.S. Pat. No. 5,580,737, entitled "High-Affinity Nucleic Acid Ligands That Discriminate Between Theophylline and Caffeine," describes a method for identifying highly specific nucleic acid ligands able to discriminate between closely related molecules, termed "counter-SELEX". U.S. patent application Ser. No. 08/143,564, filed Oct. 25, 1993, entitled "Systematic Evolution of Ligands by EXponential Enrichment: Solution SELEX," now abandoned (See U.S. Pat. No. 5,567,588), describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," now abandoned (See U.S. Pat. No. 5,660,985), that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/117,911, supra, describes highly specific nucleic acid ligands containing one or more nucleotides modified with 2'-amino (2'-NH$_2$), 2'-fluoro (2'-F), and/or 2'-O-methyl (2'-OMe).

Members of the integrin superfamily of cell adhesion receptors are known to recognize the peptide arginineglycine-aspartic acid sequence (RGD). Integrin gpIIbIIIa is a protein expressed on activated platelets which mediates platelet adhesion to fibrinogen and fibrin clots (Phillips et al. (1988) Blood 71:831; Frojmovic et al. (1991) Blood 78:369). When gpIIbIIIa binds a RGD-containing ligand, a signal is generated which triggers platelet granule release, shape change, aggregation and adhesion (Loftus et al. (1990) Science 249:915; Ware et al. (1993) N. Eng. J. Med. 328:628). Inhibitors of gpIIbIIIa-mediated platelet clot formation may have therapeutic potential in a variety of vascular diseases including reducing the occurrence of heart attacks following angioplasty.

Currently known integrin inhibitors are limited by a lack of specificity. The development of a high specificity integrin inhibitor which does not crossreact with other integrin proteins would have significant therapeutic potential.

Human neutrophil elastase (HNE or elastase) is a major protein stored in the azurophilic granules of human polymorphonuclear granulocytes (Dewald et al. (1975) J. Exp. Med. 141:709) and secreted upon inflammatory stimuli (Bonney et al. (1989) J. Cell. Biochem. 39:47). Elastase is a serine protease with a broad substrate specificity able to digest many of the macromolecules found in connective tissue such as elastin, type III and type IV collagen, and fibronectin. In addition to connective tissue components, many plasma proteins such as immunoglobulins, clotting factors, and complement proteins can also be hydrolyzed by elastase.

An excess of elastase activity has been implicated in various disease states, such as pulmonary emphysema (Kaplan et al. (1973) J. Lab. Clin. Med. 82:349; Sanders and Moore (1983) Am. Rev. Respir. Dis. 127:554), cystic fibrosis, rheumatoid arthritis (Barrett (1978) Agents and Actions 8:11), chronic bronchitis, bronchopulmonary dysplasia in premature infants, and adult respiratory distress syndrome (ARDS) (Weiland et al. (1986) Am. Rev. Respir. Dis. 133:218). In most cases, the pathogenesis of these diseases has been correlated with the inactivation or the insufficiency of natural inhibitors of elastase, which have the primary role of keeping excess elastase activity under control.

The development of an elastase-specific inhibitor has been a major therapeutic goal of the pharmaceutical industry for some time. While different types of elastase inhibitors have been developed, most of them appear to be nonspecific inhibitors of other serine proteases as well (Hemmi et al. (1985) Biochem. 24:1841). A method for developing an elastase-specific inhibitor and such an inhibitor would be highly desirable.

BRIEF SUMMARY OF THE INVENTION

Herein described is a method for generating blended nucleic acid ligands comprised of functional unit(s) added to provide a nucleic acid ligand with additional functions. In the preferred embodiment, the functional unit provides additional affinity or a desired effect such as inhibition or induction between the blended nucleic acid ligand and the target molecule. This method for combining nucleic acids with other functional groups to use in molecular evolution is herein referred to as blended SELEX.

The method of this invention provides novel means for generating nucleic acid ligands with specifically selected functionalities. For example, high affinity ligands are generated by the method of this invention which are highly specific inhibitors of a target enzyme.

The present invention encompasses nucleic acid ligands coupled to a non-nucleic acid functional unit. In one example of the blended nucleic acid ligand generated by the method of this invention, a peptide-conjugated nucleotide was produced by coupling the peptide Gly-Arg-Gly-Asp-Thr-Pro (SEQ ID NO: 1) to the derivatized base 5-(3- aminoallyl)-uridine triphosphate (RGD-UTP). RGD-UTP containing oligonucleotides (RGD-RNA) were generated by the method of this invention and shown to bind the RGD-binding protein integrin gpIIbIIIa. It is expected that RGD-RNA is a highly specific inhibitor of gpIIbIIIa.

In another example of the blended nucleic acid ligands produced by the method of this invention, a blended nucleic acid ligand to elastase with the ability to specifically inhibit elastase activity was generated. An inhibitory peptide was coupled to a single-stranded DNA ligand to elastase and the blended nucleic acid ligand shown to specifically inhibit elastase activity.

DETAILED DESCRIPTION OF THE INVENTION

Figure 1A:
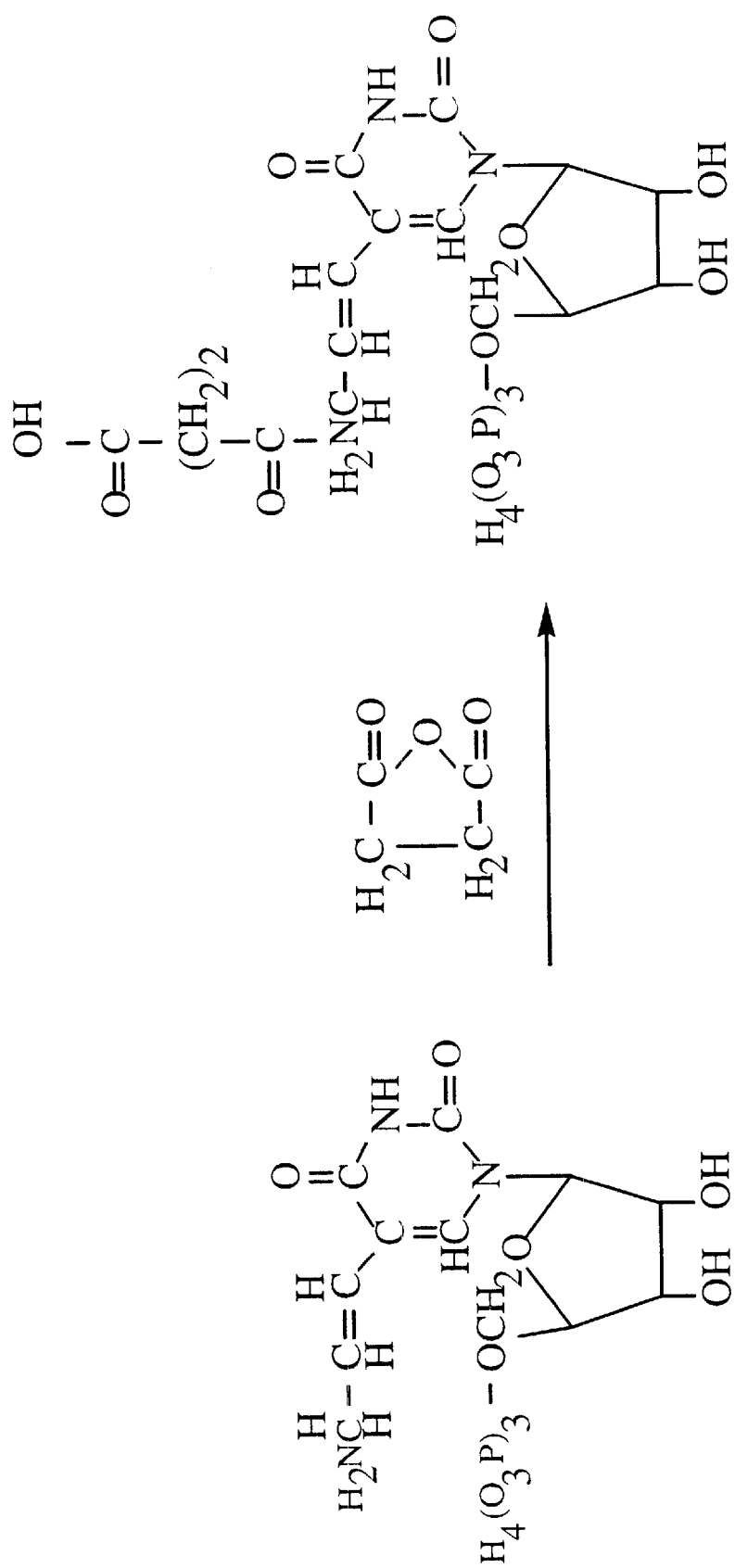
FIG. 1 illustrates the structure of 5-(3-aminoallyl)-uridine triphosphate (AA-UTP) and the synthetic scheme for production of Arg-Gly-Asp-UTP (RGD-UTP). Details of the reaction conditions are as described in Example 1.

This application describes methods for generating blended nucleic acid ligand molecules. Examples of blended nucleic acid libraries and molecules generated by these methods are provided. The methods herein described are based on the SELEX method. SELEX is described in U.S. patent application Ser. No. 07/536,428, entitled "Systematic Evolution of Ligands by EXponential Enrichment," now abandoned, U.S. Pat. No. 5,475,096, entitled "Nucleic Acid Ligands," U.S. Pat. No. 5,270,163, entitled "Methods for Identifying Nucleic Acid Ligands," (see also WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

The present invention includes a method for generating high affinity blended nucleic acid ligands to specific target molecules. The method generates blended nucleic acid molecules comprised of at least one functional unit.

Functional units that can be coupled to nucleotides or oligonucleotides include peptides, amino acids, aliphatic groups and lipid chains, or larger compounds such as peptide motifs, recognizable by the target molecule. These non-nucleic acid components of oligonucleotides may fit into specific binding pockets to form a tight binding via appropriate hydrogen bonds, salt bridges, or van der Waals interactions.

In certain embodiments of this invention, the blended nucleic acid ligands generated by the method of this invention may guide SELEX-generated ligands to specific sites of the target molecule. Further blended nucleic acid ligands may be prepared after the SELEX process for post-SELEX modification to add functionality to the ligand, for example, to increase RNA hydrophobicity and enhance binding, membrane partitioning and/or permeability, or to add reporter molecules, such as biotin- or fluorescence-tagged reporter oligonucleotides, for use as diagnostics. Blended nucleic acid ligands may be generated by the addition of chemical groups which covalently react and couple the SELEX ligand to the target molecule; in addition, catalytic groups can be added to nucleic acids to aid in the selection of SELEX ligands with protease or nuclease activity. The functional units may also serve as toxins or radiochemicals that are delivered to specific locations in the body determined by the specificity of the SELEX devised nucleic acid ligand.

Blended nucleic acid ligands are defined herein as comprising at least one nucleic acid ligand and at least one functional unit. A nucleic acid ligand is defined as any nucleic acid identified generally according to the SELEX process as described in the SELEX Patent Applications. The functional unit may be any chemical species not naturally associated with nucleic acids, and may have any number of functions as enumerated herein.

In one preferred embodiment of the invention, the blended nucleic acid ligand is prepared by performing the SELEX method utilizing an initial candidate mixture wherein each nucleic acid sequence of the candidate mixture contains at least one function unit, or a "blended candidate mixture". This may be accomplished using a candidate mixture wherein each nucleic acid sequence of the candidate mixture has 1) a single functional unit attached at either the 5' or 3' end of nucleic acid sequence, 2) functional units at both the 5' and 3' ends of the nucleic acid sequence, 3) functional units added to individual nucleic acid residues, 4) functional units attached to all or a portion of all pyrimidine or purine residues, or functional units attached to all or a portion of all nucleotides of a given type. The functional units may also be attached only to the fixed or to the randomized regions of each nucleic acid sequence of the candidate mixture.

In an alternate preferred embodiment of the invention, one or more functional units may be attached to a nucleic acid ligand identified according to the SELEX method wherein a blended candidate mixture is not used. Again the points of attachment of the functional unit(s) to the nucleic acid ligand may vary depending on the ultimate requirements for the blended nucleic acid ligands.

The examples below describe methods for generating the blended nucleic acid ligands of the present invention. As these examples establish, nucleotides and oligonucleotides containing a new functional unit are useful in generating blended nucleic acid ligands to specific sites of a target molecule.

Two examples are described for coupling peptide molecules to SELEX nucleic acid ligands in order to target specific peptide binding pockets. In the first example, a peptide containing the sequence arginine-glycine-aspartic acid (RGD) is coupled to a nucleotide and enzymatically incorporated into unselected polyribonucleotide. The RGD-containing peptide is recognized and bound by the gpIIbIIIa integrin protein, causing gpIIbIIIa-mediated platelet aggregation. A SELEX RGD-nucleic acid ligand may be generated with high specificity for gpIIbIIIa that would not crossreact with other integrins such as receptors for fibronectin, vitronectin, collagen, or laminin. SELEX blended nucleic acid ligands containing the RGD peptide could bind at or near the gpIIbIIIa ligand site and specifically inhibit gpIIbIIIa activity.

Figure 1B:
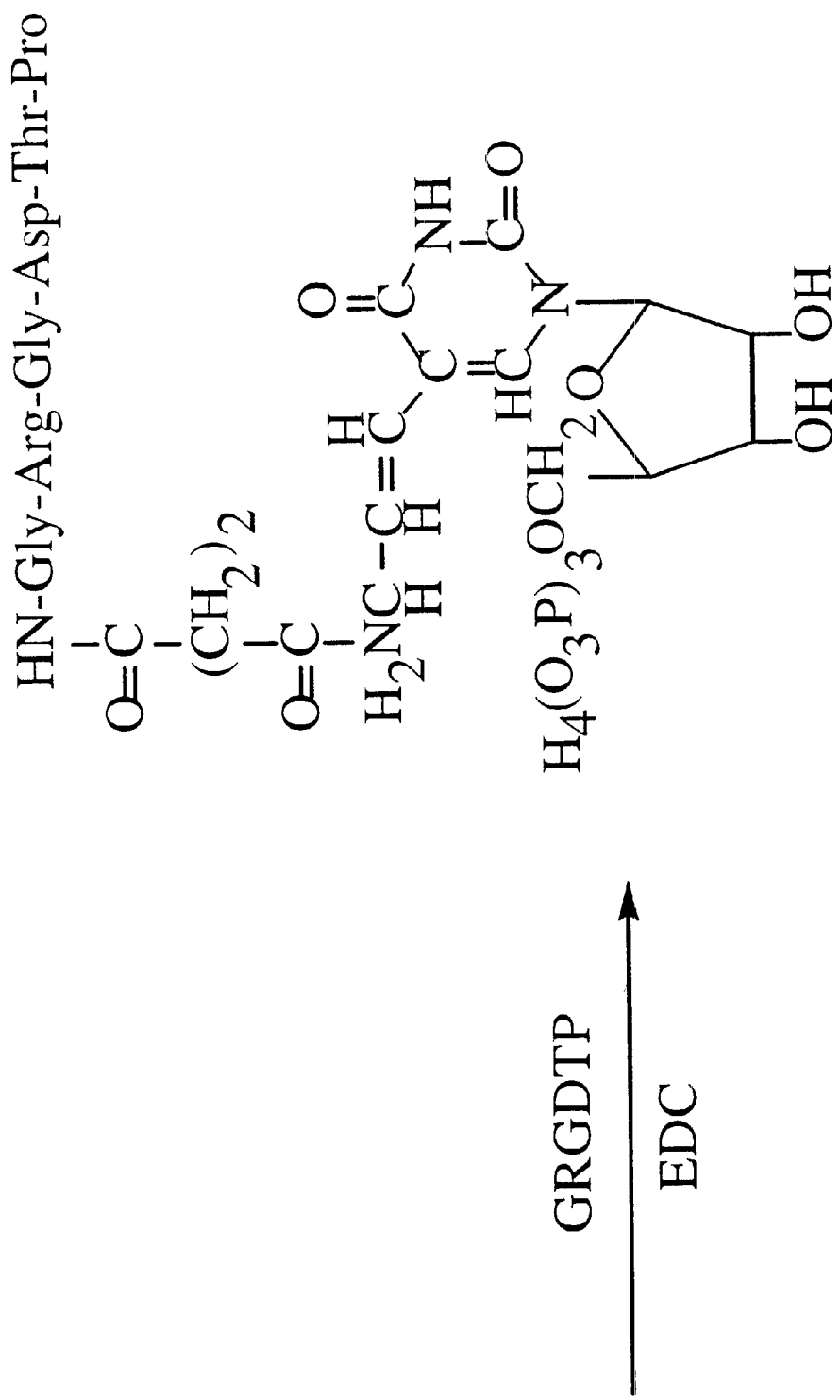

Example 1 describes the generation of a peptide-conjugated RNA. The peptide Gly-Arg-Gly-Asp-Thr-Pro (SEQ ID NO: 1) was coupled to the derivatized base, 5-(3-aminoallyl)-uridine triphosphate to produce the peptide-conjugated UTP (RGD-UTP), as shown in FIG. 1. RGD-UTP may be used in SELEX T7-catalyzed template-dependent transcription to produce an RNA oligonucleotide containing the RGD peptide at every uridine position. The Gly-Arg-Gly-Asp-Thr-Pro (SEQ ID NO: 1) peptide was chosen because the Arg-Gly-Asp (RGD) motif in matrix proteins is recognized and bound specifically by proteins of the integrin superfamnily of cell adhesion receptors. Integrins bind to such proteins as fibronectin, laminin and vitronectin, at sites containing the RGD sequence. This binding is inhibited by short RGD-containing peptides which bind integrin proteins with a Kd of approximately $10^5$ M.

Because of the specificity of RGD-containing peptides for integrins, the inventors of this application concluded that an RGD-containing peptide conjugated to an oligonucleotide may facilitate selection of high-affinity ligands to a RGD-binding target molecule. However, according to this embodiment of the invention utilizing a blended candidate mixture, peptide-conjugated oligonucleotides must also be compatible with the SELEX method: the peptide-conjugated nucleotide must be incorporated with reasonable efficiency into transcribed RNA; partitioned RNA in turn must be reasonably efficiently transcribed into complementary DNA for amplification and additional rounds of SELEX. The Examples below demonstrate that all of the conditions required for successful SELEX identification of nucleic acid ligands containing new functional groups are met by the method of this invention. The peptide-UTP derivative was enzymatically incorporated into a blended RNA oligonucleotide as shown by increased size and altered charge compared with the native or unmodified oligonucleotide and by the UV shoulder at 310 nm.

Example 2 describes the binding of RGD-RNA to RGD-binding integrin gpIIbIIIa. After separation, the bound RGD-RNA was reversed transcribed into DNA using normal SELEX protocols. The efficient transcription, partitioning, and reverse transcription shows that the site-directed blended nucleic acid ligands of this invention are compatible with the basic SELEX procedure.

A second example of the method of the present invention describes a DNA SELEX ligand coupled to a peptide inhibitor known to bind elastase.

Example 3 describes the generation of a highly specific elastase inhibitor by the method of the present invention. A SELEX-identified single stranded DNA ligand to elastase was produced and coupled to inhibitory substrate peptide chloromethyl ketone. A description of the isolation of DNA ligands to elastase and specific ligands to elastase are provided in U.S. Pat. No. 5,472,841, entitled, "Methods for Identifying Nucleic Acid Ligands of Human Neutrophil Elastase," incorporated specifically herein by reference. The resulting blended nucleic acid ligand was shown to specifically inhibit elastase.

The methods described herein do not include all of the schemes for introducing non-nucleic acid functional units, such as peptides, into an oligonucleotide. However, such methods would be well within the skill of those ordinarily practicing in the art. Putting a peptide on every uridine, as done in Example 1, has several advantages as compared with other labelling methods for use in the SELEX procedure. First, the peptide is introduced throughout both the random and fixed regions, so that evolved RNA ligands could bind close to the peptide binding site. Second, distributing the peptide at multiple sites does not restrict the geometry of RNA and does not interfere with SELEX identification of the optimal peptide position. Third, one can use pre-derivatized nucleotides with SELEX. Post-transcription modification may require additional time and expertise and introduces the additional variable of coupling efficiency.

Other methods for,coupling non-nucleic acid functional units to nucleic acids may be used to yield evolved ligands with a non-overlapping spectrum of binding sites. For instance, a peptide could be placed at the 5' or 3' end of SELEX identified RNA ligands. Another embodiment of this invention for introducing a non-nucleic acid functional unit at random positions and amounts is by use of a template-directed reaction with non-traditional base pairs. This method uses molecular evolution to select the best placement of the non-nucleic acid group on the SELEX identified ligand. For example, a X-dY base pair could be used, where X is a derivatizable ribonucleotide and the deoxynucleotide dY would pair only with X. The X-RNA would contain the non-nucleic acid functional unit only at positions opposite dY in the dY-DNA template; the derivatized X base could be positioned in either the fixed or random regions or both, and the amount of X at each position could vary between 0–100%. The sequence space of non-evolved SELEX ligands would be increased from $N^4$ to $N^5$ by substituting this fifth base without requiring changes in the SELEX protocol.

This embodiment may be used with photo-SELEX (U.S. Pat. No. 5,736,177, specifically incorporated herein by reference), where photo-active bases are placed at random sites, and these blended ligands partitioned after photolysis, then high affinity ligands are selected with the minimum number of substituted bases needed to crosslink with the target. In the same way, functional units that react covalently at enzyme active sites, such as chloromethylketones, may be incorporated to produce irreversible enzyme inhibitors. Use of directed incorporation could be used also for post-SELEX incorporation of fluorescence tags, biotin, radiolabel, lipid groups, or to cap the oligonucleotide with a uniquely modified base for protection against nuclease digestion.

Incorporation of non-nucleic acid functional units to produce blended SELEX ligands increases the repertoire of structures and interactions available to produce high affinity binding ligands. Various types of functional units can be incorporated to produce a spectrum of molecular structures. At one end of this structural spectrum are normal polynucleic acids where the ligand interactions involve only nucleic acid functional units. At the other, are fully substituted nucleic acid ligands where ligand interactions involve only non-nucleic acid functional units. Since the nucleic acid topology is determined by the sequence, and sequence partitioning and amplification are the basic SELEX steps, the best ligand topology is selected by nucleic acid evolution.

Example 3 below describes the preparation of a blended nucleic acid ligand to elastase to act as an elastase inhibitor. N-methoxysuccinyl-Ala-Ala-Pro-Val-chloromethyl ketone (SEQ ID NO:2) is an effective irreversible inhibitor for elastase. However, the nonspecific high reactive nature of chloromethyl ketone functionality in conjunction with mM range Kd of the tetrapeptide makes the inhibitor molecule unsuitable as a therapeutic agent. The enzyme inhibition of nucleic acid ligands to elastase may be improved by coupling such ligands to the substrate tetrapeptide in a nonhydrolyzable manner such that the blended nucleic acid will inhibit the enzyme by occupying the substrate binding pocket. In such a blended nucleic acid affinity and specificity is provided by the SELEX-derived nucleic acid ligand, whereas inhibition is provided by the peptide.

In one embodiment of the invention, referred to as splint blended SELEX, the functional unit of the blended nucleic acid ligand is attached to the SELEX derived nucleic acid ligand via the attachment of the functional unit to a nucleic acid that hybridizes to a region of the nucleic acid sequence of the ligand. In the preferred embodiment, the functional unit oligonucleotide is DNA, and hybridizes to the fixed region of the nucleic acid ligand or at least a region of the nucleic acid ligand that is not involved in the binding reaction to the target.

In one variation of this embodiment, the SELEX process is accomplished by the preparation of a candidate mixture of nucleic acid sequences comprised of fixed and randomized regions. The candidate mixture also contains an oligonucleotide attached to a selected functional group. The oligonucleotide is complementary to the fixed region of the nucleic acid candidate mixture, and is able to hybridize under the conditions employed in SELEX for the partitioning of high affinity ligands from the bulk of the candidate mixture. Following partitioning, the conditions can be adjusted so that the oligo-functional unit dissociates from the nucleic acid sequences.

Advantages to this embodiment include the following: 1) it places a single functional unit, such as a peptide analog, at a site where it is available for interaction with the random region of nucleic acid sequences of the candidate mixture; 2) because the functional unit is coupled to a separate molecule, the coupling reaction must only be performed once, whereas when the functional unit is coupled directly to the SELEX ligand, the coupling reaction must be performed at every SELEX cycle. (aliquots from this reaction can be withdrawn for use at every cycle of SELEX); 3) the coupling chemistry between the functional unit and the oligonucleotide need not be compatible with RNA integrity or solubility—thus simplifying the task of coupling; 4) in cases where the functional unit forms a covalent complex with the target, the SELEX derived nucleic acid ligand portion of the selected members of the candidate mixture can be released from the target for amplification or identification; and 5) following the successful identification of a blended nucleic ligand, the tethered portion of nucleic acid can be made into a hairpin loop to covalently attach the two portions of the blended nucleic acid ligand. An example of splint blended nucleic acid ligand for human neutrophil elastase is shown in Example 4 below.

EXAMPLE 1

Synthesis of Peptide Conjugated UTP

Reagents. 5-(3-aminoallyl)-uridine 5'-triphosphate, sodium salt, was obtained from Sigma Chem. Co. (St. Louis, Mo.). Gly-Arg-Gly-Asp-Thr-Pro (SEQ ID NO:1) was obtained from GIBCO-BRL (Gaithersburg, Md.). 1-ethyl-3-(dimethylaminopropyl) carbodiimide hydrochloride (EDC) was obtained from Pierce Chemical Co. (Rockford, Ill.). Other chemicals were of highest quality available from Aldrich Chem. Co. (Milwaukee, Wis.).

Succinylation of AA-UTP. The peptide Gly-Arg-Gly-Asp-Thr-Pro (SEQ ID NO:1) was coupled to UTP via a two-step reaction through the N-terminalα-amino group of the peptide. This α-amino group is the only reactive amine in the peptide and is not required for integrin binding. Condensation with peptide carboxyl groups could function to block the aspartic acid residue, thus preventing integrin binding.

5-(3-aminoallyl)UTP (5 mg) was dissolved in 250 $\mu$l of 0.2 M sodium borate, pH 8.5. The solution was mixed with 750 $\mu$l succinic anhydride (97 mg/1.14 ml DMF) and reacted for 2 h at 4° C. An equal volume of 0.1 M triethylammonium bicarbonate, pH 7.6, was added, filtered and purified on Mono Q 5×5 anion exchange FPLC (Pharmacia). The sample was applied in 0.1 M triethylammonium bicarbonate, and eluted with a linear gradient to 1.0 M triethylammonium bicarbonate. The column was eluted at 1.0 ml/min over 20 min. The major peak was pooled, lyophilized, and taken up in dry DMF for the next reaction. The sample was analyzed by TLC by spotting on PEI-F chromatography plates (J. T. Baker) and developing with 0.2 M sodium phosphate, pH 3.5.

Figure 2A:
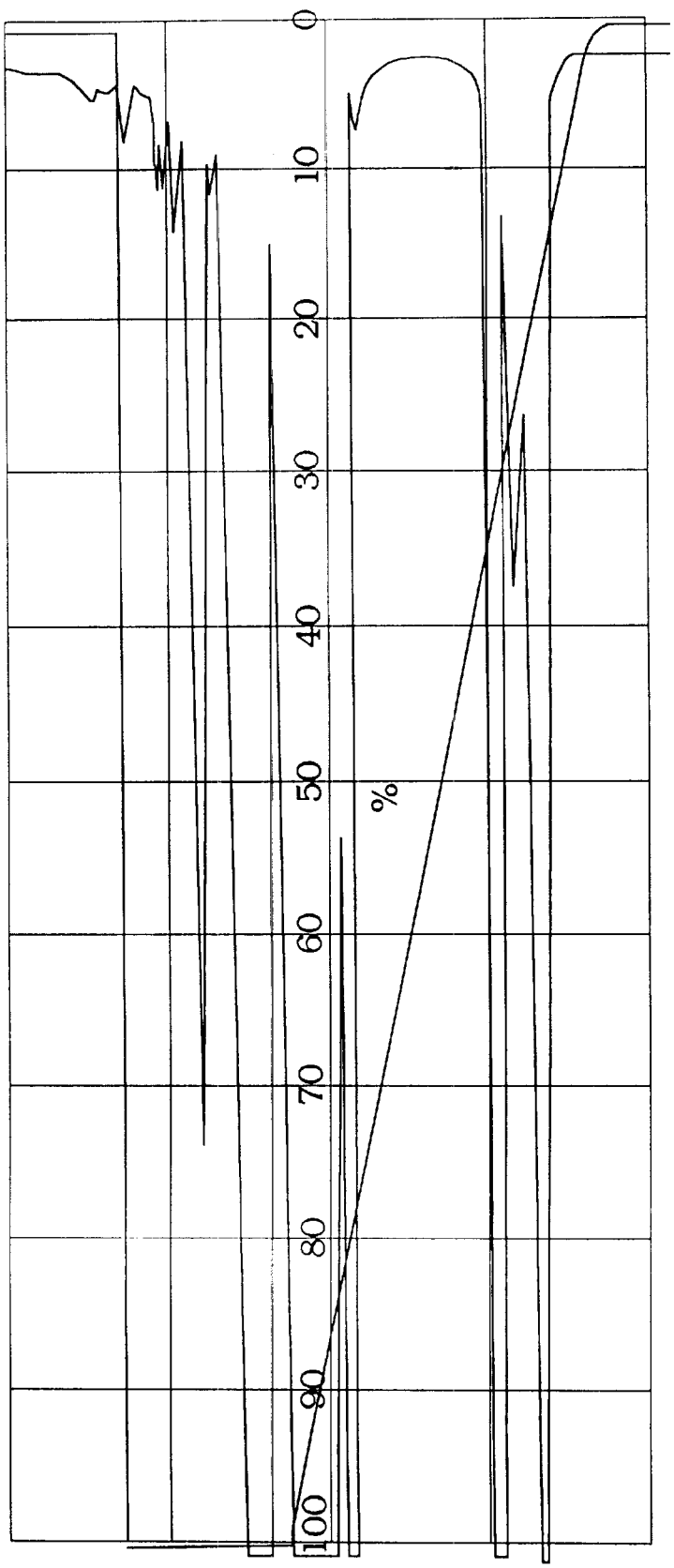
FIG. 2A shows the isolation of succinyl-UTP by Mono Q anion exchange column chromatography.
Figure 2B:
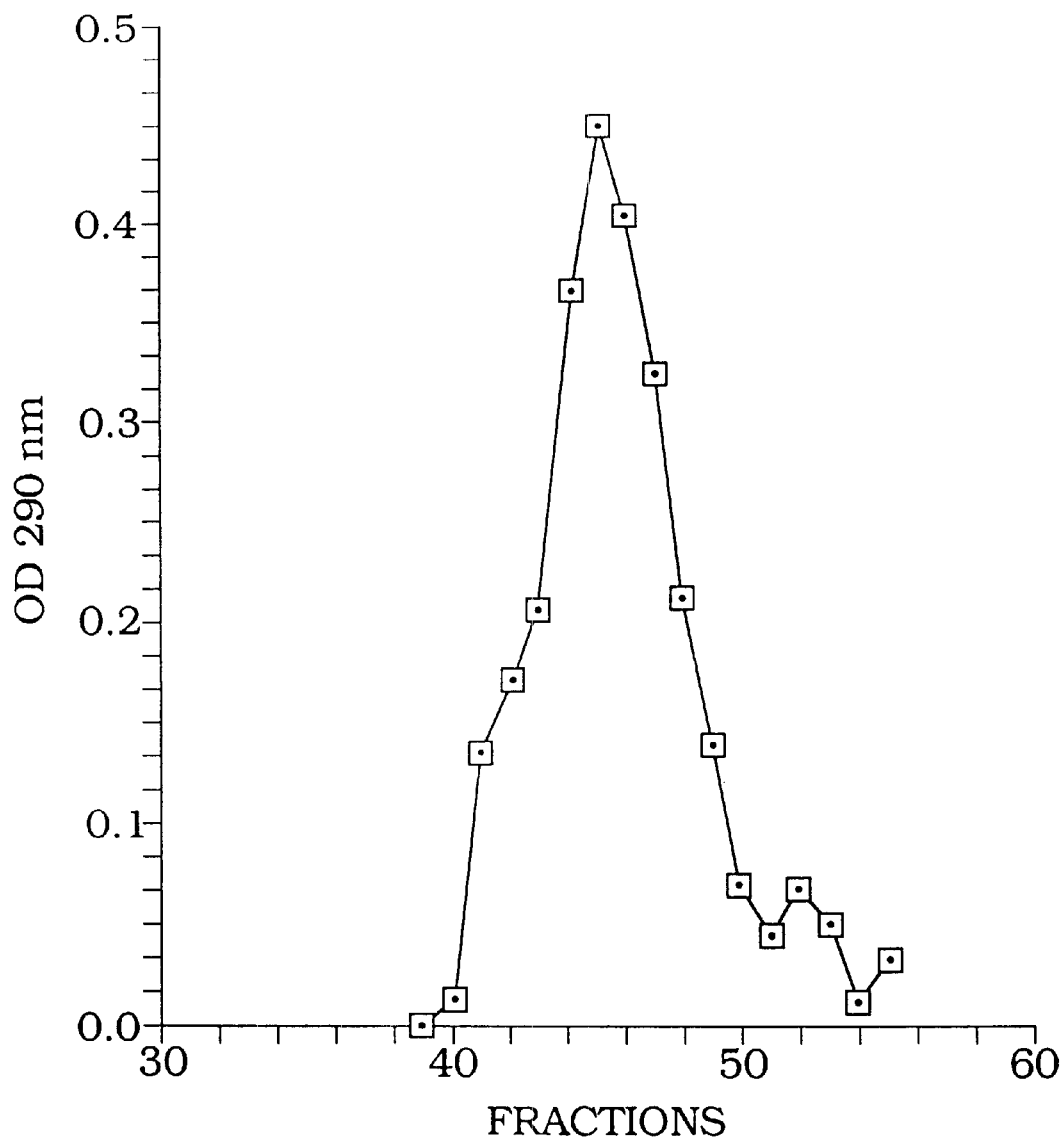
FIG. 2B shows the fractions versus the optical density at 290 nm. As described in Example 1, succinyl-UTP eluted in fractions 43–49.

Chromatographic isolation of succinyl-UTP. The succinylation reaction mixture was diluted 1:1 with 0.1 M triethylammonium-bicarbonate, pH 7.6 (Buffer A), filtered and applied to a 0.5 cm×5 cm Mono Q anion exchange column which was equilibrated with the same buffer. The column was eluted with a gradient to 1.0 M triethylammonium-bicarbonate (Buffer B) at a flow rate of 0.5 ml/ml (1 min/fraction) (FIG. 2). Succinyl-UTP was easily separated by ion exchange from the starting material. This separation is achieved because succinyl-UTP elutes from Mono Q similar to UTP, whereas AA-UTP partially neutralizes the 5'-triphosphate and elutes earlier in the salt gradient. Succinyl-UTP eluted late in the gradient from the Mono Q column (92% of Buffer B), well separated from reactants and from the AA-UTP (which eluted at approximated 68% of Buffer B). The majority of UV absorbing material eluted in the major peak, although several other peaks were present. Succinyl-UTP pooled from fractions 43–49 was lyophilized to remove the volatile buffer in preparation for the next step. The yield of this step was 80–95%. The dried sample was dissolved in dry DMF and its UV spectrum determined. This peak had the expected maximum at 290 nm.

Coupling of GRGDTP peptide to 5'(3-succinyl-aminoallyl) uridine 5'-triphosphate. The RGD peptide was condensed with succinyl-UTP using the water soluble carbodiimide. Succinyl-UTP in 58 $\mu$l of DMF was cooled to 4° C. 117 $\mu$l of N-hydroxy-succinimide (24 mg/1.4 ml DMF) was added and the mixture was reacted for 30 min at 4° C. 175 $\mu$l of EDC (0.1 M, pH 4.8) was added and the mixture reacted for 2 h at 4° C. The activated nucleotide was added to 14 mg of lyophilized GRGDTP and the mixture reacted for 2 h at 4° C. The reaction mixture was diluted 1:1 with 0.1 M triethylammonium bicarbonate, purified on a Mono Q column as above, and analyzed by TLC and Fast Atom Bombardment (FAB) Mass Spectrometry (University of Colorado Structural Division).

Figure 3A:
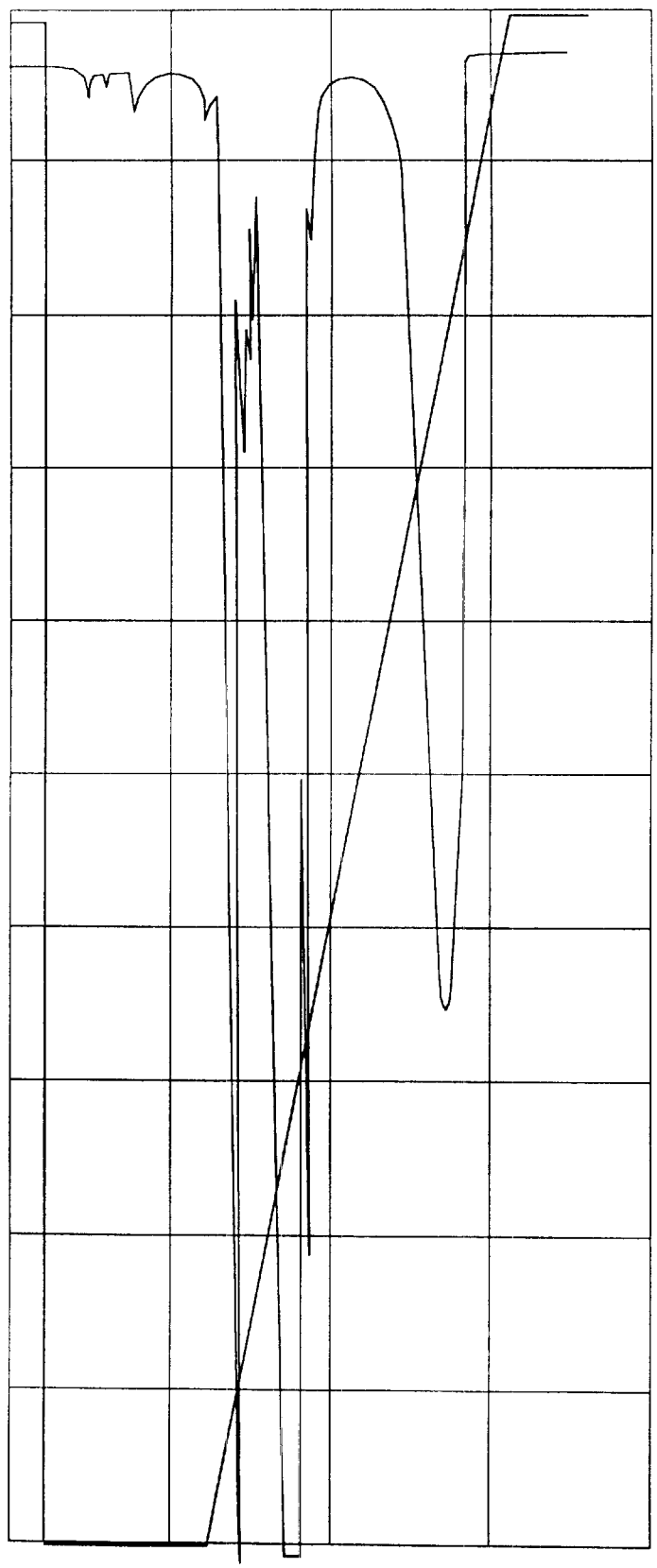
FIG. 3A shows the isolation of RGD-UTP by Mono Q anion exchange column chromatography.
Figure 3B:
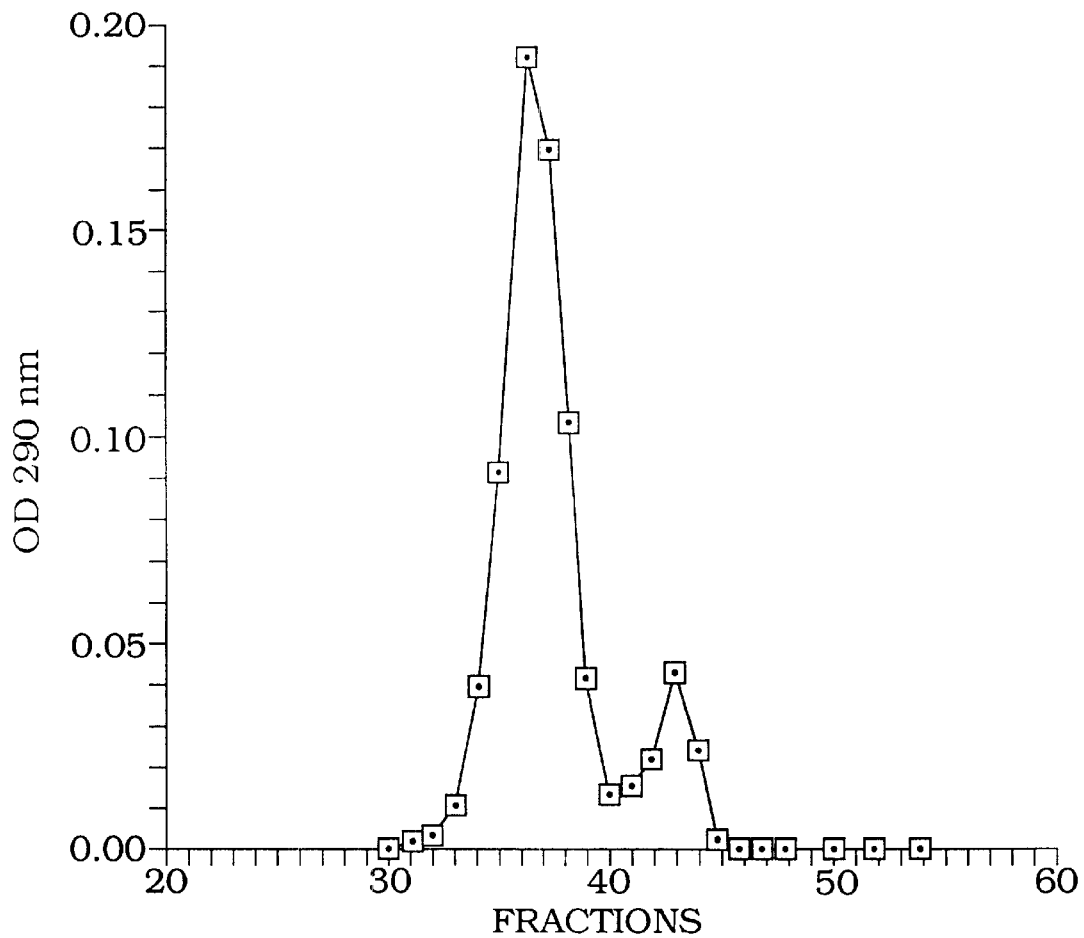
FIG. 3B shows the fractions versus the optical density at 290 nm. As described in Example 1, RGD-UTP eluted in fractions 35–38.

Chromatographic isolation of RGD-UTP. RGD-UTP was purified by ion exchange chromatography. The peptide coupling reaction mixture was diluted with Buffer A, filtered and purified on the Mono Q column described above. RGD-UTP eluted from the Mono Q column similar to AA-UTP, but ahead of succinyl-UTP, suggesting the arginine side chain also interacts with the phosphate charge. The major peak eluted at approximately 70% of Buffer B, ahead of the peak of residual succinyl-UPT (which eluted at approximately 90% of Buffer B) (FIG. 3). Only trace amounts of other peaks were detected, except for the EDC which eluted earlier. Fractions 35–38 were pooled and lyophilized. The sample was dissolved in dry DMF for thin layer chromatography (TLC) and FAB mass spectroscopy. The sample had a maximum adsorption at 290 nm.

Figure 4:
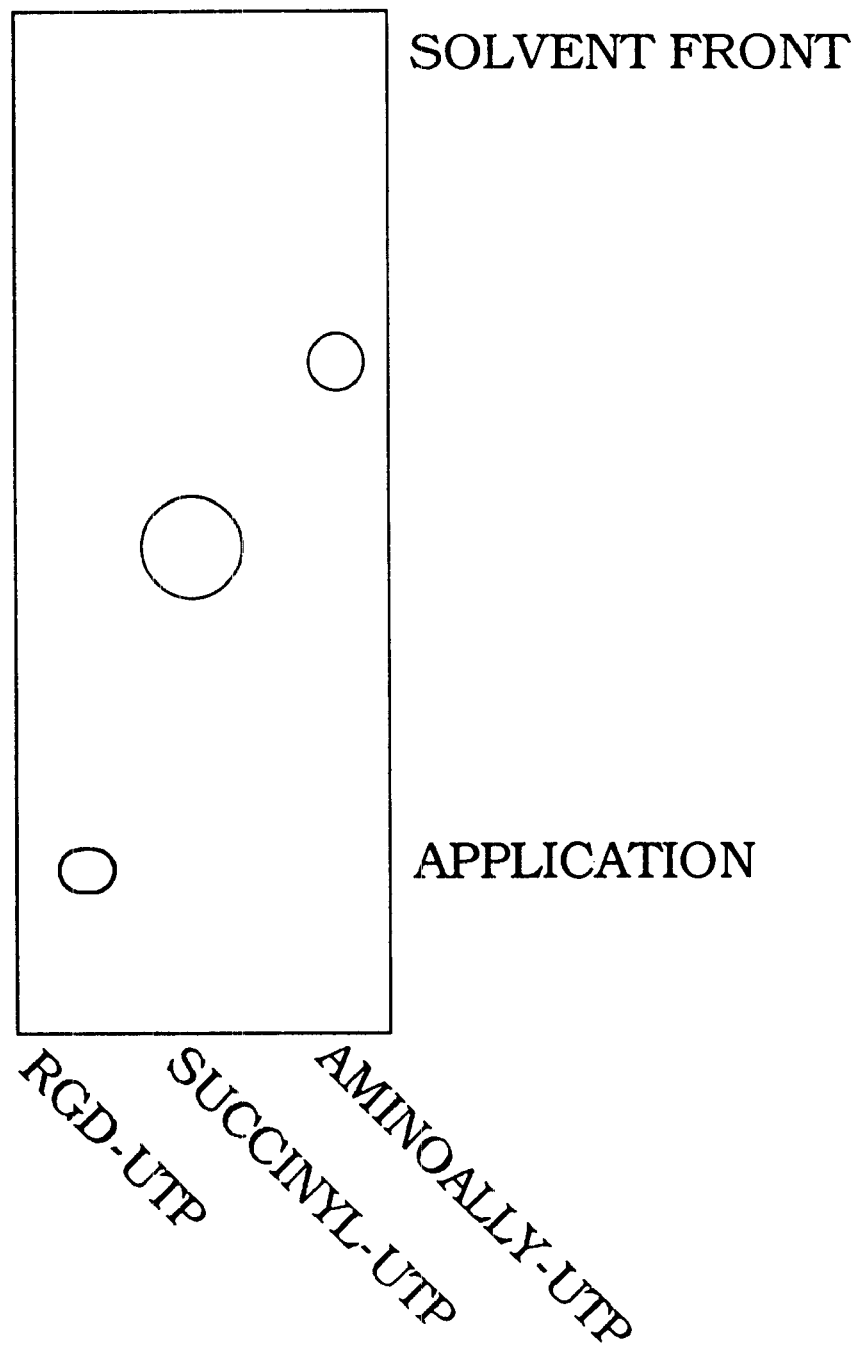
FIG. 4 shows the results of thin layer chromatography of aminoallyl-UTP, succinyl-UTP, and RGD-UTP.

Thin layer chromatography of AA-UTP, succinyl-UTP and RGD-UTP. As shown in FIG. 4, RGD-UTP is cleanly separated from both AA-UTP and succinyl-UTP. AA-UTP, succinyl-UTP, and RGD-UTP were spotted onto cellulose PEI-F TLC plates (J. T. Baker, Inc.) and developed with 0.75 M NaH$_2$PO$_4$, pH 3.5. AA-UTP migrated near the solvent front, succinyl-UTP migrated with an R$_f$ of 0.42, and RGD-UTP remained at the origin. This TLC system is an ideal method for monitoring product formation.

Mass spectrometry analysis. RGD-UTP analyzed by FAB mass spectroscopy yielded a mass of 1223, remarkably close to the calculated formula weight (FW) of 1222. The precision of the mass spectrometry result shows that RGD was coupled in the predicted manner, and that no side reactions occurred introducing alternative or additional derivatives. Further, there were no smaller peaks present which would indicate degradation or dephosphorylation of the triphosphate.

EXAMPLE 2

Binding of RGD-RNA to gpIIbIIIa

Molecular biology techniques. Agarose electrophoresis, T7 RNA transcription, and AMV reverse transcription were performed generally as described in the SELEX Patent Applications. FPLC purification of RNA oligonucleotides was achieved using a 5×5 Mono Q anion exchange column. The RNA transcription reaction mixture was phenol:chloroform extracted, ethanol precipitated and washed, and dissolved in 50 mM sodium phosphate, 0.2 M NaCl, 6 M urea, 50% formamide (Fisher, Ultrapore, low-UV absorbance), pH 6.0. Following sample application, the column was developed with a linear gradient to 1 M NaCl. The RNA peak was precipitated by addition of 2:1 v/v ethanol, the pellet was washed with 80% ethanol and dried in a speed-vac, then dissolved in SELEX binding buffer (150 mM NaCl, 10 nM HEPES, 2 mM CaCl$_2$, 1 mM MgCl$_2$, 0.1%

Tween, pH 7.4). RNA and RNA-gpIIbIIIa (Enzyme Research) complexes were prepared by incubation at 37° C. for 10 min, and separated by size exclusion chromatography on a 16×100 Superdex 200 column (Pharmacia) which was equilibrated and run in the binding buffer. Concentration and removal of detergent from the samples collected from the Superdex column was achieved by adsorption onto a Resource Q column (Pharmacia) and elution with 1 M NaCl.

Figure 5:
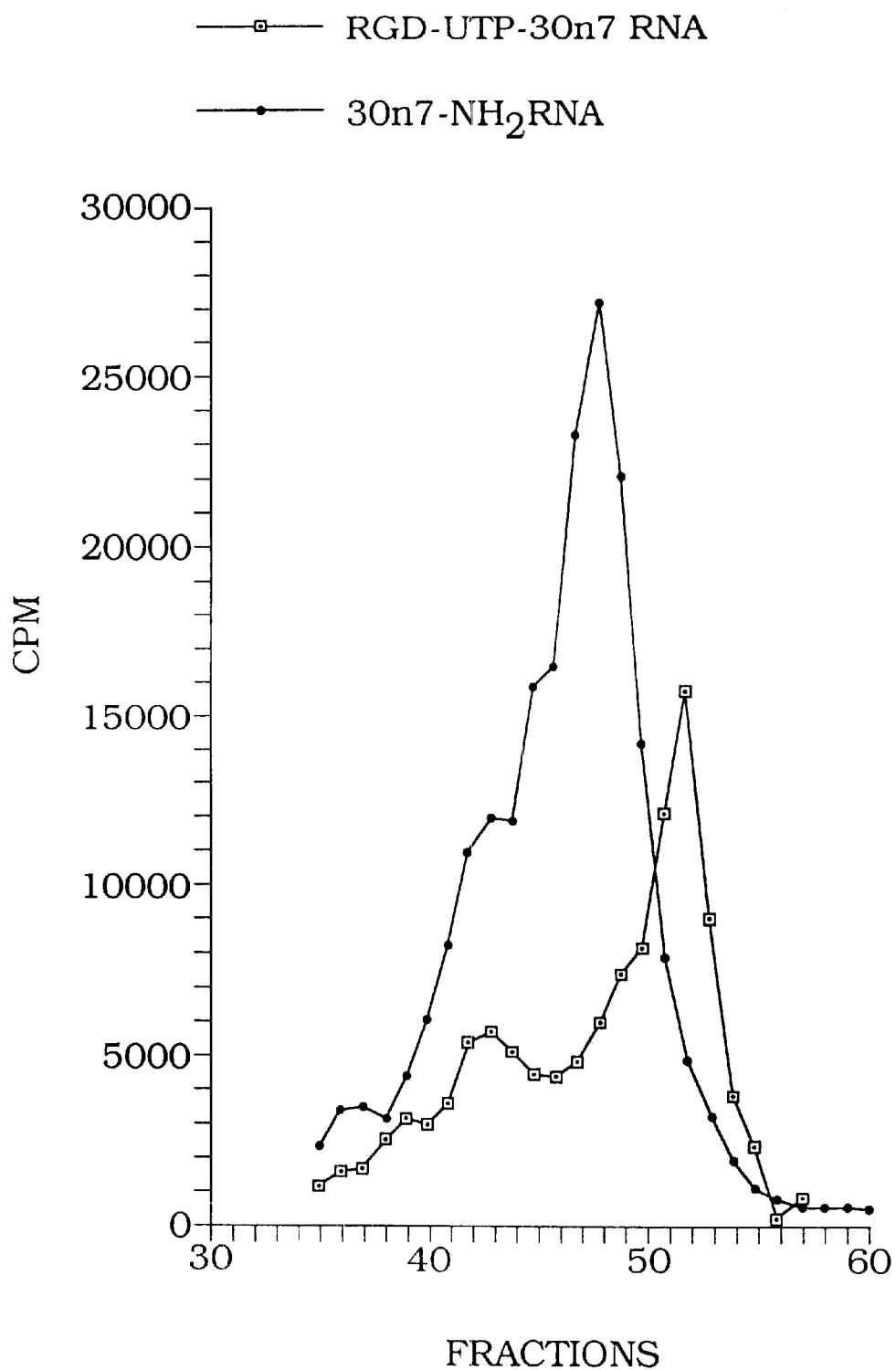
FIG. 5 shows the results of RGD-UTP RNA transcript purification by anion exchange chromatography. The elution of RGD-UTP RNA (□) and RNA (♦) from a Mono Q anion exchange column is shown.

RGD-UPT transcription and purification. RGD-UTP was used in a T7 RNA polymerase reaction by direct substitution for normal UTP, and gave yields that were at least 50% of those obtainable with UTP. The concentration of RGD-UTP and other NTPs was 1 mM; the DNA template contained 5' and 3' fixed regions flanking a 30 base pair random sequence. The RNA transcript was purified by adsorption onto an anion exchange column (Mono Q)in a phosphate buffer containing 6 M urea and 50% formamide, and eluted with a gradient to 1 M NaCl (FIG. 5). RGD-RNA eluted as one major peak from the column at a position in the gradient slightly ahead of the elution position of an equivalent RNA transcript made with normal UTP, consistent with the altered charge and perhaps altered conformation of the derivatized RNA. The amount of truncated RNA material was only slightly increased compared to normal RNA transcription.

Figure 6:
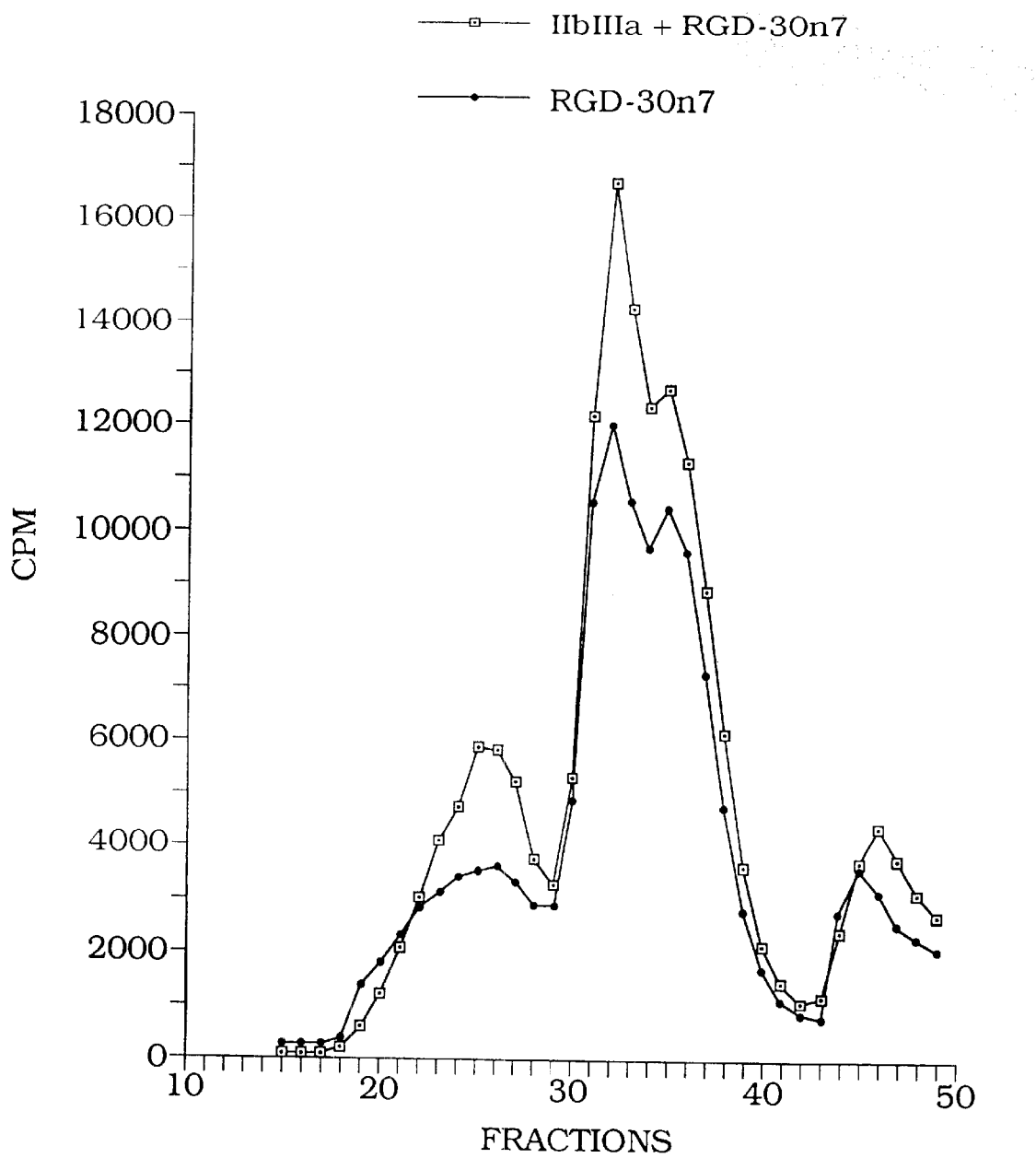
FIG. 6 shows the separation of RGD-30n7 RNA and gpIIbIIIa by size exclusion chromatography on Superdex 200 (Pharmacia). The elution profiles of RGD-30n7 bound to gpIIbIIIa (□) and RGD-30n7 (♦) are shown.

Binding of RGD-30n7 RNA to gpIIbIIIa. Size-based partitioning, used to separate RGD-RNA bound to gpIIbIIIa integrin from unbound RGD-RNA, is a method for identifying high affinity RNA ligands to gpIIbIIIa (Kd<$10^{-8}$). RGD-RNA was incubated with gpIIbIIIa (2 mg/ml) in 0.15 M NaCl, 2 mM $CaCl_2$, 20 mM $MgCl_2$, 20 mM HEPES, 0.1% Tween 20, pH 7.4. The results showed that RGD-RNA incubated with gpIIbIIIa yielded a higher molecular weight RNA peak than obtained for samples not incubated with gpIIbIIIa. Normal RNA made with UTP and partitioned in the same manner did not have the high molecular weight peak, indicating that binding to gpIIbIIIa of RNA not coupled to the RGD peptide was weaker than that of the blended molecule. The estimated molecular mass is consistent with the addition of the RGD peptide at each uridine position (FIG. 6). Perhaps more conclusively, chromatographically purified RGD-RNA had an absorbance shoulder, compared to normal RNA, at 310 nm resulting from incorporation of AA-UTP. A small peak of early eluting material was detected in the column void volume which was not present in samples of RGD-RNA chromatographed without protein. The high molecular weight RGD-RNA-gpIIbIIIa peak was concentrated and detergent removed by adsorption and elution from an anion exchange column. The RNA was reversed transcribed and PCR amplified. The DNA obtained yielded a single band of expected size on agarose electrophoresis, indicating that RGD-RNA is reverse transcribed with acceptable efficiency even with the low amounts of RNA extracted during SELEX partitioning.

EXAMPLE 3

Substrate-Coupled Selex-Derived Blended Ligands as Elastase Inhibitors

To demonstrate that a high affinity, high specificity nucleic acid ligand coupled to an inhibitor peptide is a viable method of producing a high affinity inhibitor to elastase, a ssDNA ligand to elastase was coupled to the inhibitory substrate peptide chloromethyl ketone such that the chloromethyl functionality is inactivated by creating a non-hydrolyzable linkage. ssDNA ligand 17 (DNA-17) (from U.S. Pat. No. 5,472,841, entitled, "Methods for Identifying Nucleic Acid Ligands of Human Neutrophil Elastase," having the sequence TAGCGATACTGCGTGGGT-TGGGGCGGGTAGGGCCAGCAGTCTCGT-GCGGTACTTGAGCA (SEQ ID NO:3)) has a Kd for elastase of 15 nM. Because it was not known which end of DNA-17 is in close proximity to the active site of elastase, blended nucleic acid molecules were prepared in which the substrate peptide was attached to both the 3' and 5' ends of the DNA.

Figure 7:
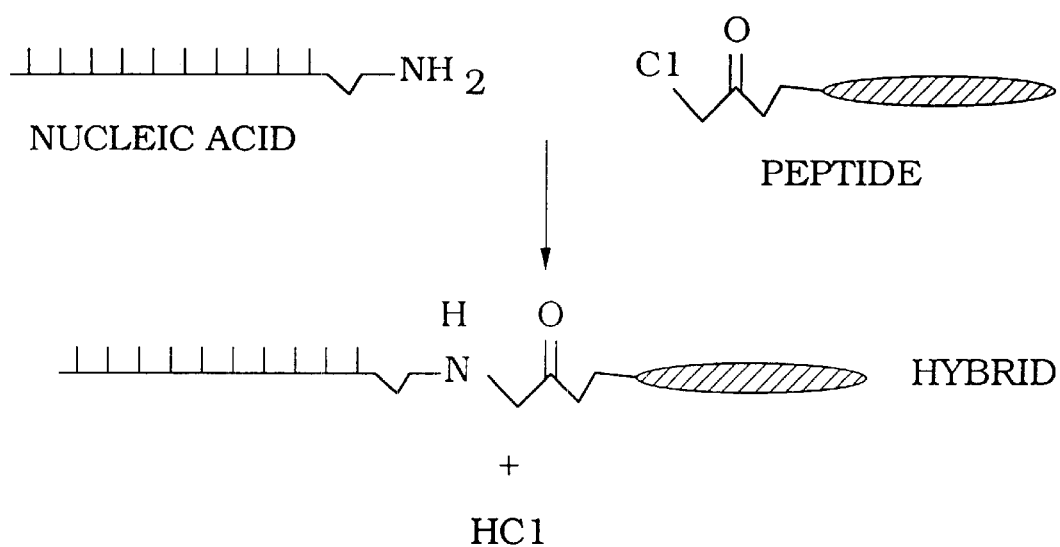
FIG. 7 shows the chemistry of the attachment of the inhibitory substrate peptide N-methoxysuccinyl Ala-Ala-Pro-Val-chloromethyl ketone (SEQ ID NO:2) to a high affinity single-stranded DNA (DNA-17).

Peptide conjugation. The chemistry of the attachment is shown in FIG. 7. An oligonucleotide with four 18-atom ethylene glycol moieties (synthesized by using spacer phosphoramidite, Clonetech) and a thiol group at the 3' end was synthesized by automated DNA synthesis, deprotected by standard methods, and gel purified. Immediately after the deprotection of the 3'-SH group, the oligonucleotide was passed through a Sephadex-G50 spin column equilibrated in 0.5 M triethylammonium acetate buffer (pH 7.5) to remove excess DTT, and then mixed with N-methoxysuccinyl Ala-Ala-Pro-Val-chloromethyl ketone (SEQ ID NO:2) (25 mg/200 µl of DMF). The mixture was incubated at 37° C. overnight. 20 µl of 1 M DTT was added to inactivate the unreacted chloromethyl ketone inhibitor. The peptide conjugated DNA was finally purified from the unconjugated peptide either by three successive Sephadex-G50 spin columns or by reverse phase HPLC.

Elastase inhibition assay. The assay for elastase inhibition is based on the use of a chromogenic tetrapeptide substrate. The assay was conducted in a buffer containing 10 nM elastase, 0.5 mM N-methoxysuccinyl-Ala-Ala-Pro-Val-p-nitroanilide (SEQ ID NO:4), 150 mM NaCl, 26 mM KCl, 2 mM $MgCl_2$, 0.02% HSA, 0.05% DMSO, 0.01% Triton X-100, and 100 mM Tris-HCl, at 25° C. The assay measured the generation of elastase-induced release of p-nitroanilide as a function of time by spectroscopy (OD 405 nm). The rate of p-nitroanilide generation in the absence of inhibitor was used as the control. Positive control was established in the presence of the irreversible inhibitor N-methoxysuccinyl-Ala-Ala-Pro-Val-chloromethyl ketone (SEQ ID NO:2).

Figure 8:
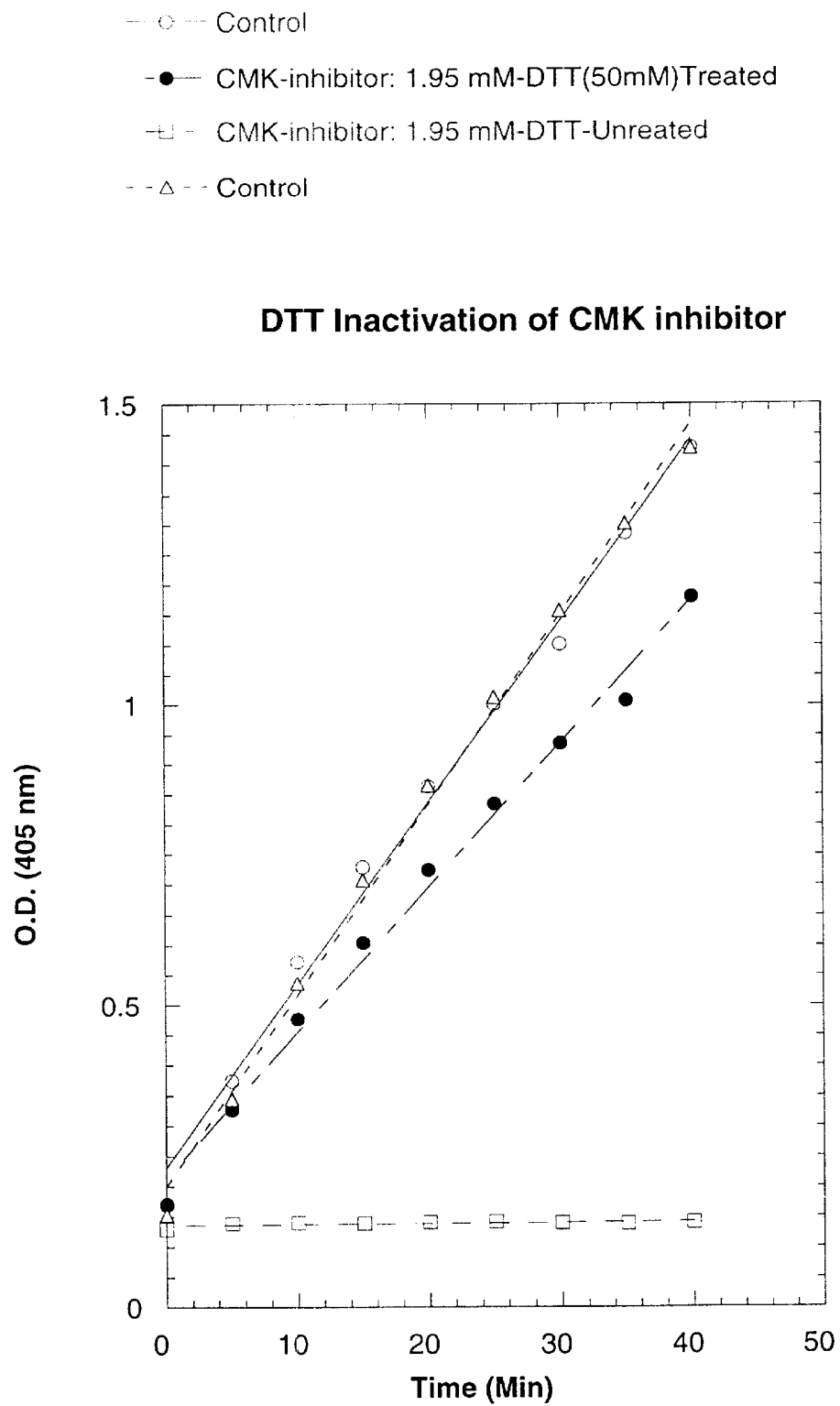
FIG. 8 shows the inactivation of 1.95 mM N-methoxysuccinyl Ala-Ala-Pro-Val-chloromethyl ketone (SEQ ID NO:2) by 50 mM DTT.

The presence of trace amounts of unreacted N-methoxysuccinyl Ala-Ala-Pro-Val-chloromethyl ketone (SEQ ID NO:2) in the final blended nucleic acid ligand preparation will inhibit the enzyme. However, this possibility will be eliminated by inactivating the inhibitor with DTT. FIG. 8 shows the inactivation of N-methoxysuccinyl Ala-Ala-Pro-Val-chloromethyl ketone (SEQ ID NO:2) by DTT. Incubation of 1.95 M N-methoxysuccinyl Ala-Ala-Pro-Val-chloromethyl ketone (SEQ ID NO:2) with 50 mM DTT destroyed the inhibition. The partial inhibition seen with the inactivated inhibitor may be due to competitive inhibition due to the high peptide concentration.

Figure 9:
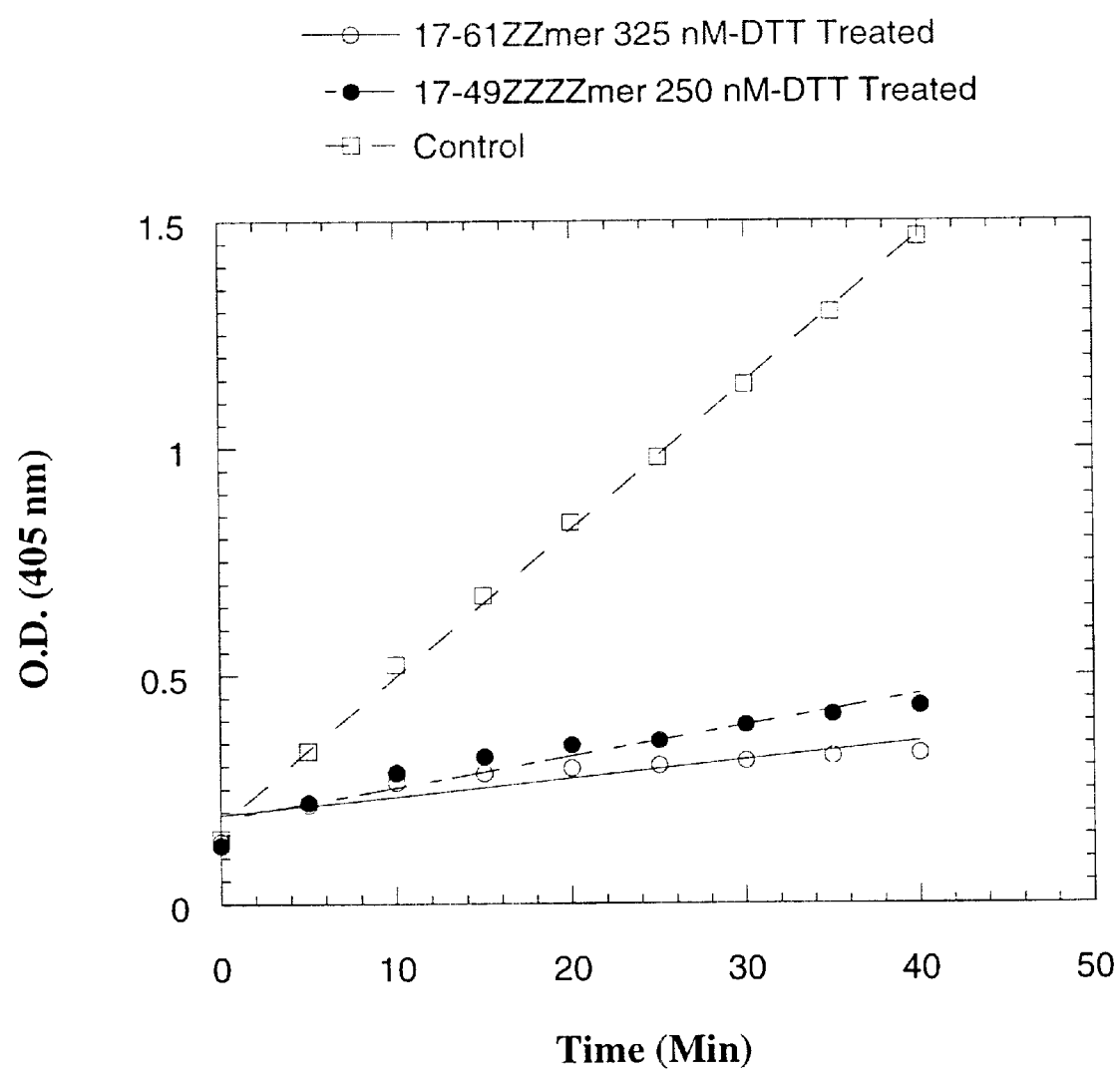
FIG. 9 shows the inhibition of the blended nucleic acid ligand in the presence of 20 mM DTT.
Figure 10:
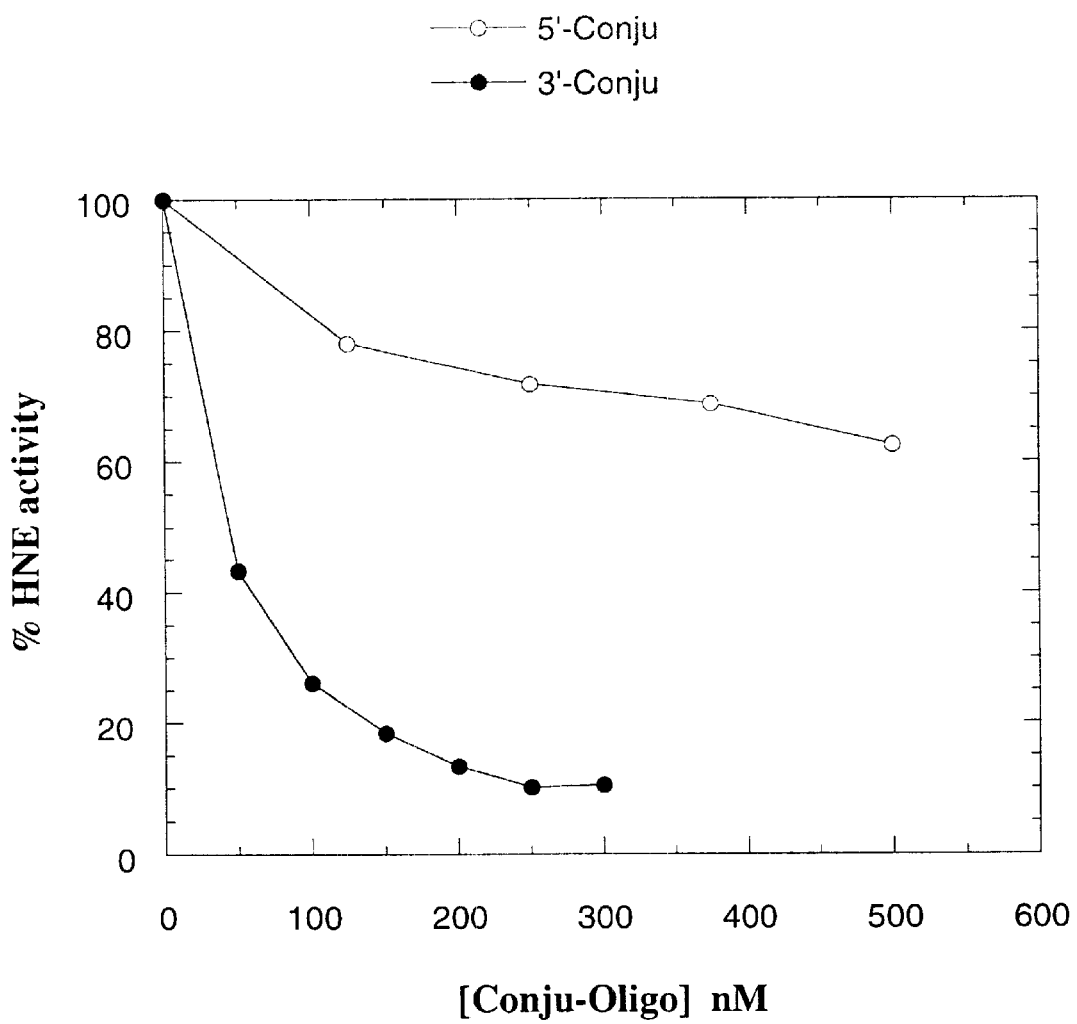
FIG. 10 shows the inhibition of elastase by DNA-17 conjugated at the 5' end with chloromethyl ketone (○), and DNA-17 conjugated at the 3' end with chloromethyl ketone (●).
Figure 11:
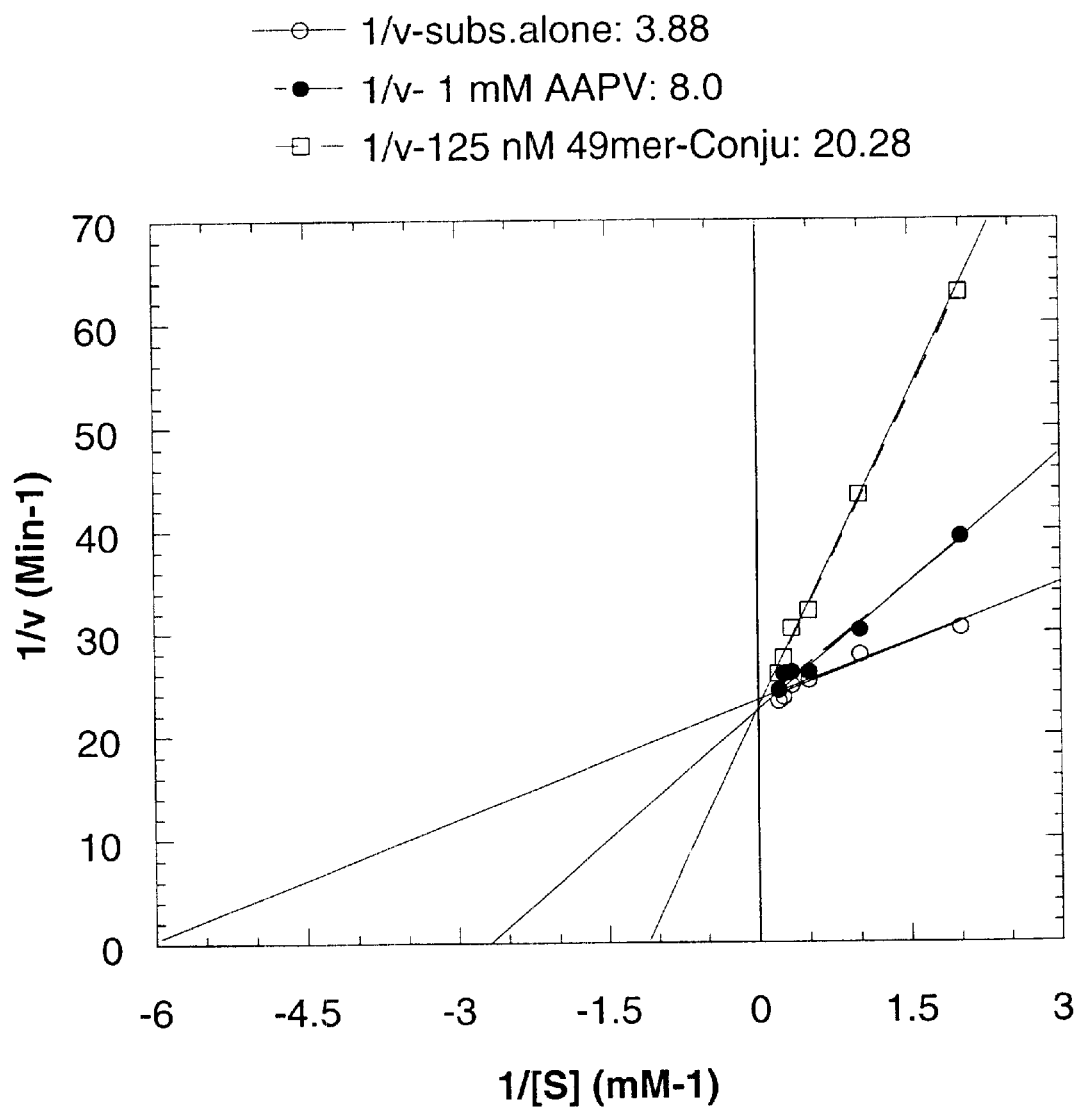
FIG. 11 is a Lineweaver-Burk plot of the inhibition of elastase by N-methoxysuccinyl Ala-Ala-Pro-Val (SEQ ID NO:5) (●), peptide-conjugated oligonucleotide (□) and substrate alone (○).

FIG. 9 shows the inhibition of the blended nucleic acid ligand in the presence of 20 mM DTT. The inhibition of elastase by the 5' end blended nucleic acid ligand and the 3' end blended nucleic acid ligand is shown in FIG. 10. A Lineweaver-Burk plot of elastase inhibition by N-methoxysuccinyl Ala-Ala-Pro-Val (SEQ ID NO:5) or the blended nucleic acid ligand is shown in FIG. 11. The resulting Km of 0.16 mM for the substrate is in good agreement with published values. The Ki of the blended nucleic acid ligands was 30 nM versus 920 µM for the inhibitor peptide alone, or a 30,000 fold improvement.

Figure 12A:
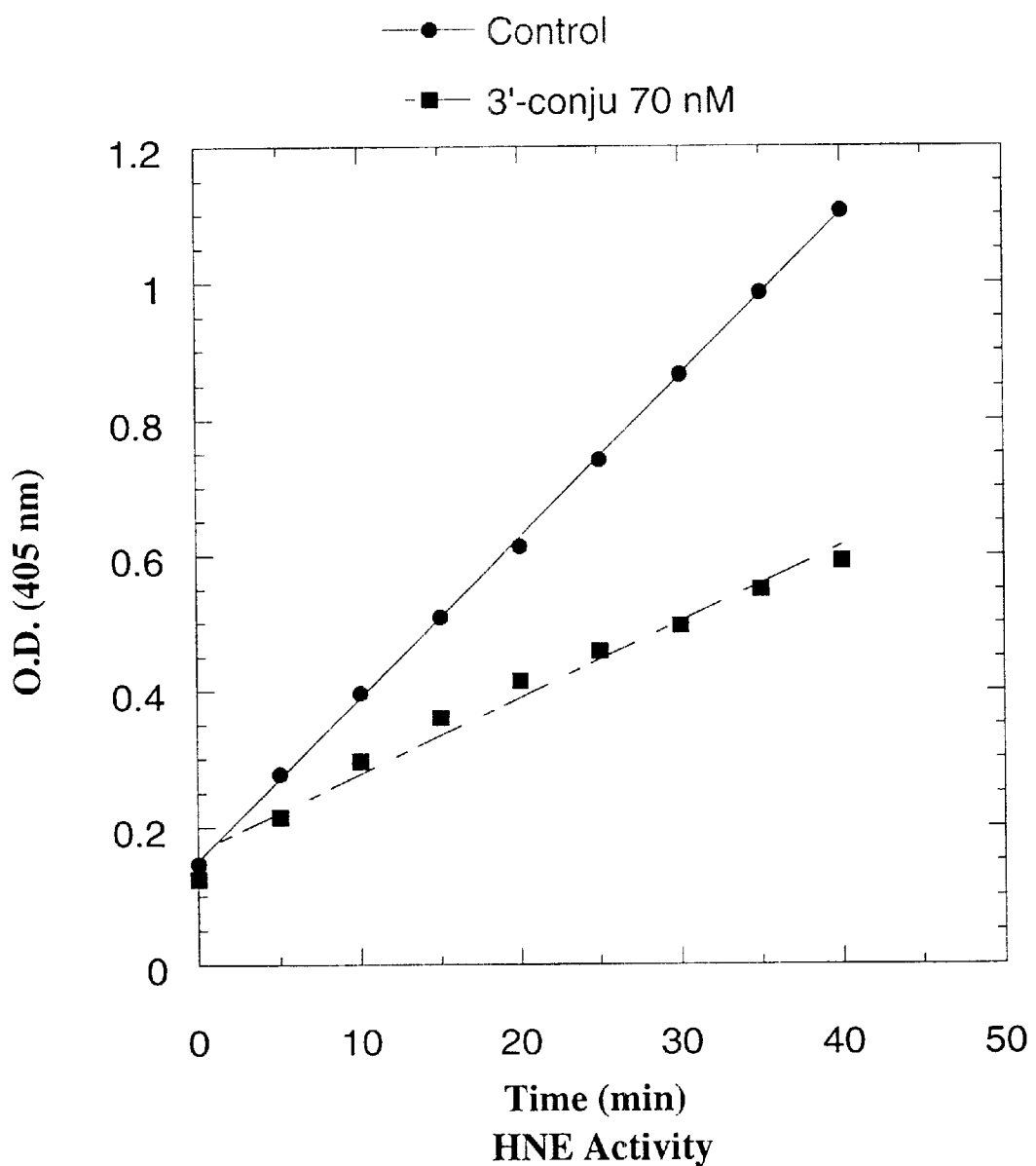
FIGS. 12A–12C show the inhibition of elastase by DNA ligands with and without the inhibitors conjugated at the 3' end compared with the effect of conjugated and non-conjugated ligands on (A) HNE Activity, (B) Urokinase Activity and (C) Thrombin Activity.
Figure 12B:
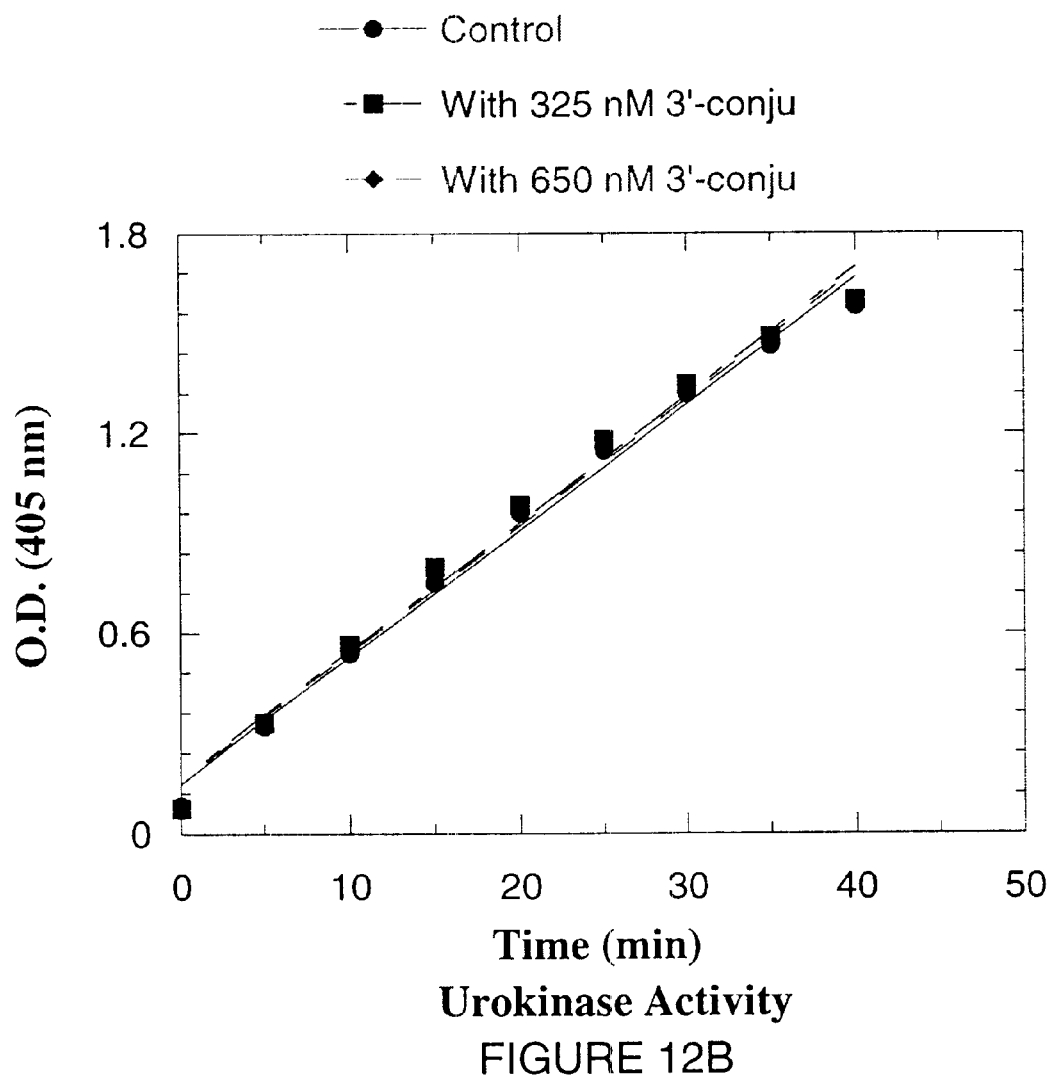
Figure 12C:
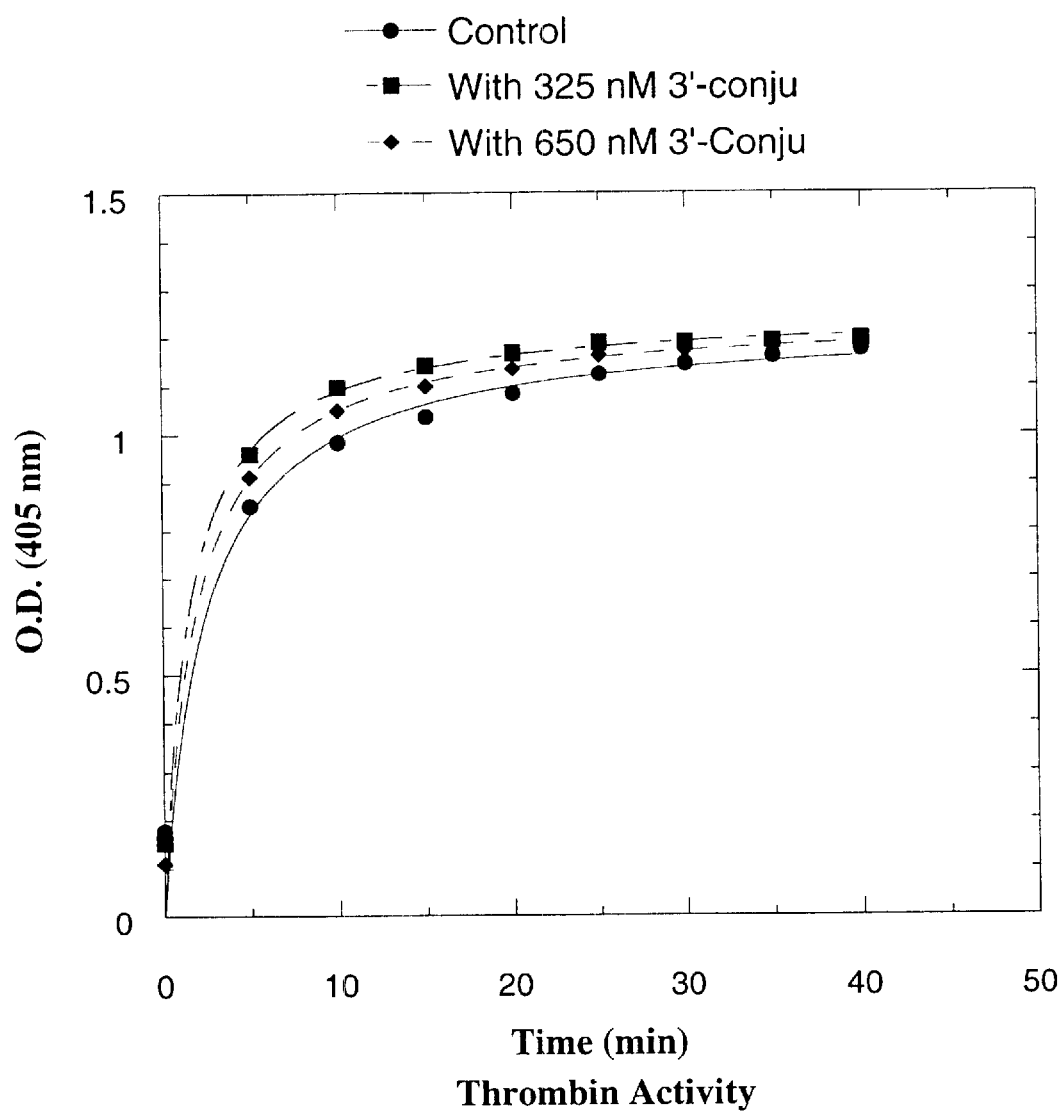

The inhibition of two other human serine proteases—urokinase and thrombin—by the 3' end blended nucleic acid DNA-17 was also examined, and shown in FIG. 12. At 70 nm concentration the 3' end blended nucleic acid has greater than 50% inhibition of elastase, whereas even at 650 nm concentration neither urokinase nor thrombin were inhibited to any detectable extent. These results demonstrate the specificity of the blended nucleic acid ligand for elastase.

EXAMPLE 4

Splint Blended SELEX.

Figure 13:
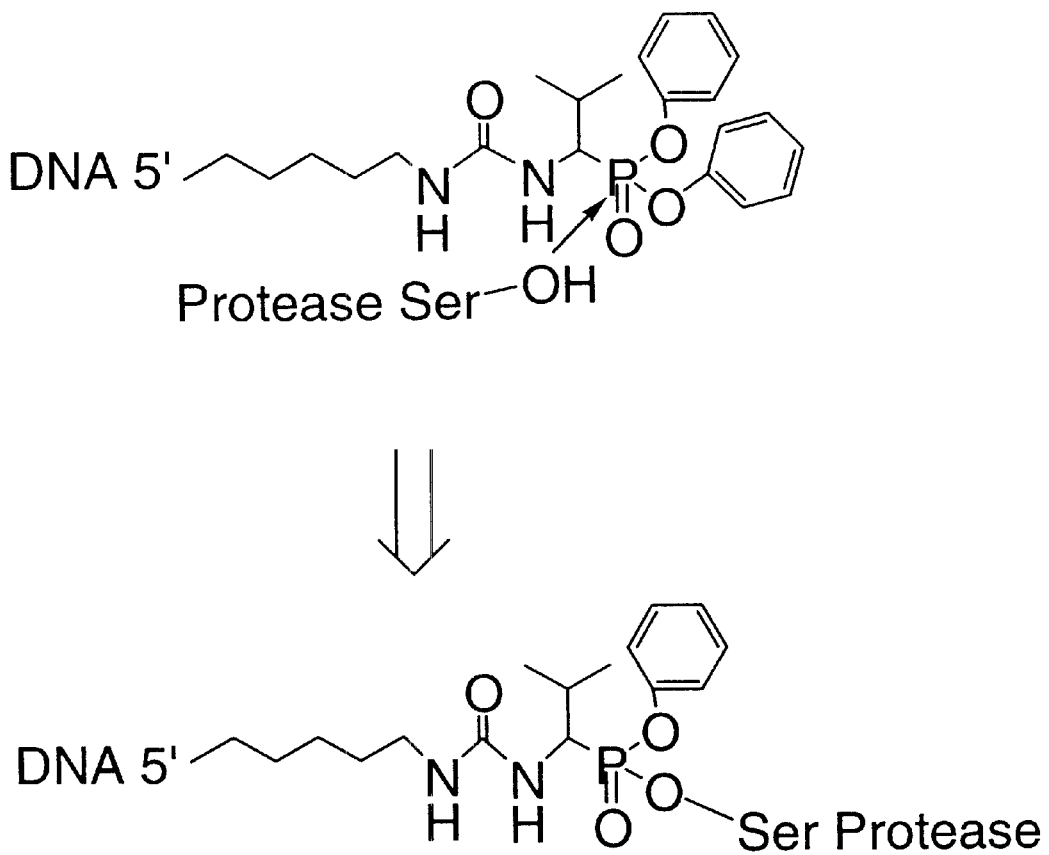
FIG. 13 depicts the valyl phosphonate moiety attached to a nucleic acid segment as used in Example 4 below, and the reaction of the species with human neutrophil elastase.

The splint blended SELEX process was performed by preparing a standard SELEX candidate mixture and a single compound containing a valyl phosphonate attached to a nucleic acid sequence that hybridizes to a portion of the fixed region of the candidate mixture of nucleic acid sequences as shown in FIG. 13. FIG. 13 also shows the chemical reaction that occurs between the valylphosphonate and human neutrophil elastase (HNE).

The valyl phosphonate was activated via an NHS ester. This compound was coupled to the 5' hexyl amine linker of a 19-mer DNA oligo complementary to the 5'-fixed region of 40N7.1. A candidate mixture composed of pyrimidine 2'NH$_2$-substituted RNA was hybridized to the splint, and reacted with HNE at subsaturating protein concentrations. Covalent complexes were enriched by diluting the reaction 100-fold, then filtering through nitrocellulose.

Figure 14:
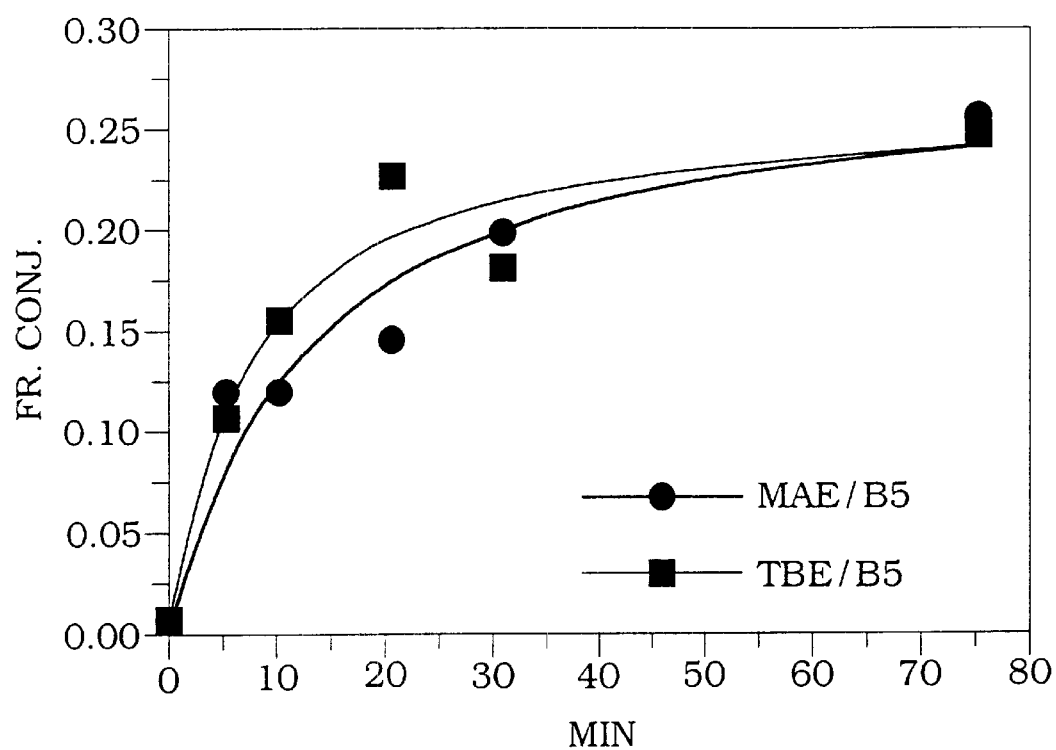
FIG. 14 depicts the first order rate constant of a pool of splint blended SELEX nucleic acid ligands after five rounds of SELEX measured by gel electrophoresis; TBE pH 8 (■) and MAE pH 6 (●).

After five rounds of selection for species that reacted with the HNE, the reactivity of the pool was assayed by gel electrophoresis (5% polyacrylamide/TBE pH 8 or MAE pH 6/0.25% SDS). The results are shown in FIG. 14. The analysis of reaction rates indicates biphasic kinetics, with $k_1obs \cong 0.1$ min$^{-1}$, and $k_2obs \cong 0.01$ min$^{-1}$. The reaction plateaus at 30%, presumably because the valyl phosphonate is a racemic mixture and the theoretical limit is 50%. A $k_1obs$ of 0.1 min$^{-1}$ at a protein concentration of 50 nM indicates a second order rate constant $\geq 2 \times 10^6$ M$^{-1}$min$^{-1}$. The reported rate constant for the valyl phosphonate alone is $10^3$–$10^4$ M$^{-1}$min (Oleksyszyn et at. (1989) Biophys. Biochem. Res. Comm. 161: 143–149). Thus, the splint blended nucleic acid mixture increases the reaction rate of the species by at least $10^3$ fold. The reaction of the selected pool is also highly specific. No reaction of the pool with thrombin, another serine protease, is detectable. The second-order rate constant for the thrombin reaction is estimated to be <200 M$^{-1}$min$^{-1}$, $10^4$ fold lower than the reaction rate with elastase.

What is claimed is:

1. A blended nucleic acid ligand of a target compound, wherein the nucleic acid ligand is identified from a blended candidate mixture comprised of blended nucleic acids each having at least one nucleic acid region and at least one functional unit, according to the method comprising:
   a) contacting the blended candidate mixture with the target, wherein blended nucleic acids having an increased affinity to the target relative to the blended candidate mixture may be partitioned from the remainder of the blended candidate mixture;
   b) partitioning the increased affinity blended nucleic acids from the remainder of the blended candidate mixture; and
   c) amplifying the increased affinity blended nucleic acids to yield a ligand-enriched mixture of blended nucleic acids, whereby a blended nucleic acid ligand of the target compound may be identified.

2. A diagnostic reagent comprising the blended nucleic acid ligand of claim 1.

3. The diagnostic reagent of claim 2 wherein said at least one functional unit is a reporter molecule.

4. The diagnostic reagent of claim 3, wherein the reporter molecule is a post-method modification.

5. The diagnostic reagent of claim 3, wherein the reporter molecule is biotin.

6. The diagnostic reagent of claim 3, wherein the reporter molecule is a fluorescent tagged oligonucleotide.

7. A method for identifying a diagnostic reagent of a target from a blended candidate mixture comprised of blended nucleic acids each having at least one nucleic acid region and at least one functional unit, said method comprising:
   a) contacting the blended candidate mixture with the target, wherein blended nucleic acids having an increased affinity to the target relative to the blended candidate mixture may be partitioned from the remainder of the blended candidate mixture;
   b) partitioning the increased affinity blended nucleic acids from the remainder of the blended candidate mixture;

c) amplifying the increased affinity blended nucleic acids to yield a ligand-enriched mixture of blended nucleic acids, whereby a diagnostic reagent of a target may be identified.

8. The method of claim 7 further comprising adding a reporter molecule to the diagnostic reagent.

9. The method of claim 7 wherein said at least one nucleic acid region is composed of a fixed region and a randomized region.

10. The method of claim 9 wherein said at least one functional unit is attached to an oligonucleotide hybridized to said fixed region.

11. A diagnostic reagent identified according to the method of claim 7.

12. A method for preparing a diagnostic reagent, wherein said diagnostic reagent comprises a blended nucleic acid ligand of a target compound and a reporter molecule, comprising:

a) identifying a nucleic acid ligand of a target compound from a candidate mixture comprised of nucleic acids each having a region of randomized sequence by a method comprising: i) contacting the candidate mixture with the target, wherein nucleic acids having an increased affinity to the target relative to the candidate mixture; ii) partitioning the increased affinity nucleic acids from the remainder of the candidate mixture, and iii) amplifying the increased affinity nucleic acids to yield a ligand-enriched mixture of nucleic acids, whereby a nucleic acid ligand of the target compound may be identified;

b) attaching at least one functional unit to said nucleic acid ligand to yield a blended nucleic acid ligand of the target compound; and c) attaching at least one reporter molecule to said blended nucleic acid ligand, whereby a diagnostic reagent is prepared.

* * * * *